US011981751B2

(12) United States Patent
Kang et al.

(10) Patent No.: US 11,981,751 B2
(45) Date of Patent: *May 14, 2024

(54) METHOD OF CONTROLLING ADHESION AND POLARIZATION OF MACROPHAGES BY USING NANOBARCODE

(71) Applicant: Korea University Research and Business Foundation, Seoul (KR)

(72) Inventors: Heemin Kang, Seoul (KR); Young Keun Kim, Seoul (KR); Sunhong Min, Seoul (KR); Yoo Sang Jeon, Seoul (KR); Hyojun Choi, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/246,403

(22) Filed: Apr. 30, 2021

(65) Prior Publication Data

US 2021/0363182 A1 Nov. 25, 2021

(30) Foreign Application Priority Data

May 22, 2020 (KR) .................. 10-2020-0061704
Jun. 5, 2020 (KR) .................. 10-2020-0068517

(51) Int. Cl.
*C07K 5/08* (2006.01)
*C07K 5/09* (2006.01)
*C12N 5/0786* (2010.01)

(52) U.S. Cl.
CPC .......... *C07K 5/0817* (2013.01); *C12N 5/0645* (2013.01)

(58) Field of Classification Search
CPC ....... C07K 5/0817; C12N 5/0645; B82Y 5/00
See application file for complete search history.

(56) References Cited

U.S. PATENT DOCUMENTS

2019/0008187 A1 1/2019 Konda et al.

FOREIGN PATENT DOCUMENTS

| JP | 2003-529128 A | 9/2003 |
| JP | 2019-194581 A | 11/2019 |
| KR | 10-2018-0039724 A | 4/2018 |
| KR | 10-2034381 B1 | 10/2019 |

OTHER PUBLICATIONS

Sharma (A Dissertation submitted to the faculty of University of Minnesota, 2015) (Year: 2015).*
Japanese Office Action dated Oct. 11, 2022 for corresponding Japanese Patent Application No. 2021-064766, 10 pages; with English machine translation.
Sharma, A. "Multi-segmented magnetic nanowires as multifunctional theranostic tools in nanomedicine," A Dissertation submitted to the faculty of University of Minnesota, 2015, pp. 180 and 224-225; cited in NPL No. 1.
Tomioka, H et al. "M1 and M2 Macrophage Populations: Those Induced and Activated by Mycobacterial Infections," Kekkaku, Feb. 2016, pp. 75-82, vol. 91, No. 2; cited in NPL No. 1; with English Abstract.
Office Action dated Mar. 29, 2022, for corresponding Japanese Patent Application No. 2021-064766; with English machine translation.
Anirudh Sharma, "Multi-segmented magnetic nanowires as multifunctional theranostic tools in nanomedicine," A Dissertation submitted to the faculty of University of Minnesota, Jul. 2015, pp. 1-12 and 131-159; cited in NPL No. 1.
Yoo Sang Jeon et al., "Metallic Fe—Au Barcode Nanowires as a Simultaneous T Cell Capturing and Cytokine Sensing Platform for Immunoassay at the Single-Cell Level," ACS Applied Materials & Interfaces, Jun. 12, 2019, vol. 11, Issue 27, pp. 23901-23908; cited in NPL No. 1.
Daniel E. Shore et al., "Enrichment and Quantification of Epitope-specific CD4+T Lymphocytes using Ferromagnetic Iron-gold and Nickel Nanowires, " Scientific Reports, Oct. 24, 2018, vol. 8, Article No. 15696; cited in NPL No. 1.
Jeemin Kang et al., "Anisotropic Ligand Nanogeometry Modulates the Adhesion and Polarization State of Macrophages," Nano Letters, ACS Publications, American Chemical Society, 2019, 13 Pages, cited in NPL 2.
Korean Office Action dated Aug. 5, 2021, in connection with the corresponding Korean Patent Application No. 10-2020-0068517.
Heemin Kang et al., "Immunoregulation of macrophages by dynamic ligand presentation via ligand-cation coordination," Nature Communications, Apr. 12, 2019, vol. 10, No. 1696.

* cited by examiner

*Primary Examiner* — Sudhakar Katakam
(74) *Attorney, Agent, or Firm* — Hauptman Ham, LLP

(57) ABSTRACT

Disclosed are a nanobarcode for controlling adhesion and polarization of macrophages and a method of controlling adhesion and polarization of macrophages by using nanobarcodes. The method of controlling adhesion and polarization of macrophages of the present invention may efficiently control adhesion and phenotypic polarization of macrophages in vivo or in vitro by tuning periodicity and sequences of ligand peptide (RGD) of a nanobarcode.

5 Claims, 19 Drawing Sheets
(9 of 19 Drawing Sheet(s) Filed in Color)

FIG. 14

METHOD OF CONTROLLING ADHESION AND POLARIZATION OF MACROPHAGES BY USING NANOBARCODE

CROSS REFERENCE TO RELATED APPLICATION

This present application is based upon and claims the benefit of priority to Korean Patent Application No. 10-2020-0061704 filed on May 22, 2020, and Korean Patent Application No. 10-2020-0068517 filed on Jun. 5, 2020 in the Korean Intellectual Property Office. The disclosures of the above-listed applications are hereby incorporated by reference herein in their entireties.

TECHNICAL FIELD

The present invention relates to a nanobarcode for controlling adhesion and polarization of macrophages and a method of controlling adhesion and polarization of macrophages by using the nanobarcode, and more particularly, to a method of controlling adhesion and polarization of macrophages by using a substrate presenting the nanobarcode.

BACKGROUND ART

A macrophage is the main cell responsible for innate immunity. Most of the macrophages are fixed in the whole body, but some of the macrophages are present in the form of monocytes in the blood. The monocytes may be divided into dendritic cells or macrophages. Most of the macrophages are fixed, representatively include dust cells, microglial cells, Kupffer cells, and Langerhans cell, and the like, and the macrophages are distributed throughout the body. When antigens invade, the macrophages eat the antigens or secrete toxins to destroy and remove the antigens, and deliver antigens to lymphocytes and trigger an immune response. When an enemy invades the wound, the monocytes in the blood go out of the blood vessels like neutrophils and are divided into macrophages to remove bacteria. Further, the macrophages are divided into a free form which moves to various places in the body and performs phagocytosis, and a fixed form which is fixed to designated organs and performs phagocytosis. The macrophages in the fixed form include liver Kupffer cells, alveolar macrophages, connective tissue structure (histiocyte), and brain microglia cells, and the like.

As described above, as a method of efficiently controlling the regeneration and anti-inflammatory effects of macrophages, a technology through the presentation of ligands in vivo is used. However, there is a problem in that the existing micro-scale integrin ligand peptide (RGD) uncaging controls the adhesion of host macrophages, but does not control the functional phenotypic polarization of macrophages.

PRIOR ART LITERATURE

Patent Document

Korean Patent Application Laid-Open No. 2018-0039724

SUMMARY OF THE INVENTION

To solve the aforementioned problems, the present invention provides a nanobarcode coated with a ligand, and a method of controlling adhesion and polarization of macrophages by tuning periodicity and sequences of ligands coated on the nanobarcode.

An exemplary embodiment of the present invention provides a nanobarcode for controlling adhesion and polarization of macrophages, the barcode including: a nanobarcode in which a first segment including iron (Fe) and a second segment including gold (Au) are repeatedly formed; and an integrin ligand peptide bound to the second segment of the nanobarcode.

Another exemplary embodiment of the present invention provides a method of preparing the nanobarcode for controlling adhesion and polarization of macrophages, the method including: preparing a nanobarcode in which a first segment including iron (Fe) and a second segment including gold (Au) are repeatedly formed; substituting a carboxylate substituent on the first segment by mixing the nanobarcode and a first suspension; and mixing the nanobarcode and a second suspension including integrin ligand peptide (RGD).

Still another exemplary embodiment of the present invention provides a method of controlling adhesion and polarization of macrophages, the method including: manufacturing a nanobarcode-presenting substrate by putting a substrate of which a surface is activated in a solution containing the nanobarcode for controlling adhesion and polarization of the macrophage, and controlling adhesion and polarization of the macrophage after treating the nanobarcode-presenting substrate with a culture medium.

The nanobarcode for controlling adhesion and polarization of macrophages according to the present invention tunes periodicity and sequences of ligand peptide coated on the nanobarcode, thereby easily controlling adhesion and phenotypic polarization of the macrophages.

Further, the method of controlling adhesion and polarization of macrophages according to the present invention applies a magnetic field to a substrate including the nanobarcode, thereby performing reversible control and efficiently controlling adhesion and phenotypic polarization of the macrophages in vivo or in vitro.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 is an immunofluorescent confocal image (a) of a substrate including the nanobarcode according to the exemplary embodiment of the present invention for iNOS, F-actin, and nucleus cultured for 36 hours in the M1 polarization medium, and an immunofluorescent confocal image (b) of substrate including the nanobarcode according to the exemplary embodiment of the present invention for Arg-1, F-actin, and nucleus cultured in an M2 polarization medium with and without inhibitors for ROCK (Y27632), myosin II (blebbistatin), or actin polymerization (cytochalasin D), and in this case, a scale bar represents 20 μm.

DETAILED DESCRIPTION

Hereinafter, to describe the present invention more specifically, an exemplary embodiment of the present invention will be described in more detail with reference to the accompanying drawings. However, the present invention is not limited to the exemplary embodiment described herein, and may also be specified in other forms.

The present invention provides a nanobarcode for controlling adhesion and polarization of macrophages including: a nanobarcode in which a first segment containing iron (Fe) and a second segment containing gold (Au) are repeatedly formed; and integrin ligand peptide bound to the second segment of the nanobarcode.

Figure 1:
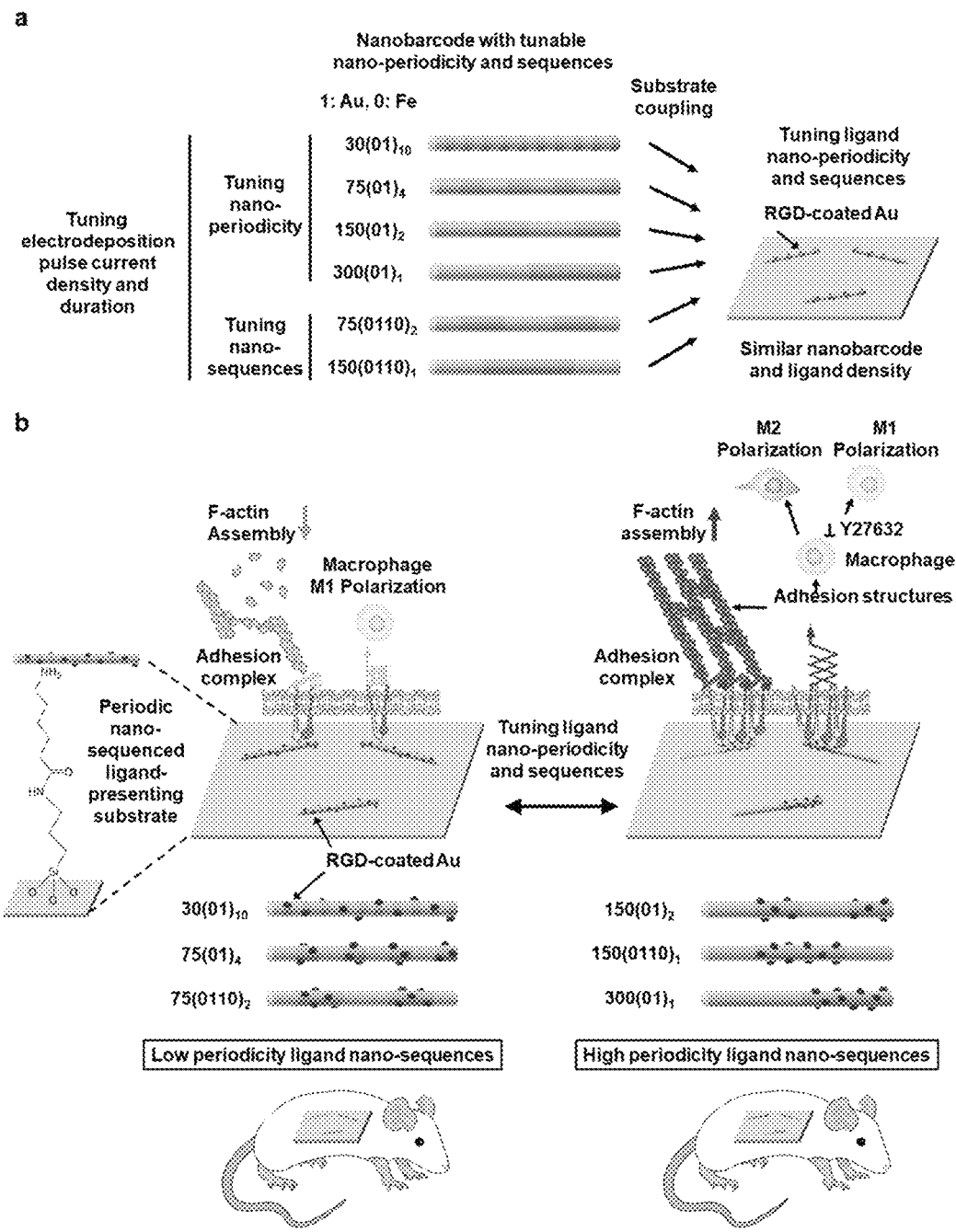
FIG. 1 is a schematic diagram illustrating a nanobarcode substrate for controlling adhesion and polarization of macrophages and a method of controlling adhesion and polarization of macrophages by using the nanobarcode substrate according to an exemplary embodiment of the present invention.

FIG. 1 is a schematic diagram illustrating a nanobarcode for controlling adhesion and polarization of macrophages, a substrate coupled with the nanobarcode, and a method of controlling adhesion and polarization of macrophages by using the same according to an exemplary embodiment of the present invention.

Referring to FIG. 1, it can be seen that the nanobarcode of the present invention includes: a nanobarcode in which a first segment containing iron (Fe) and a second segment containing gold (Au) are repeatedly formed; and an integrin ligand peptide bound to the second segment of the nanobarcode, in which the integrin ligand peptide is an integrin peptide.

In particular, the nanobarcode may be provided in a rod shape satisfying Equation 1 or Equation 2.

$$[L(M_1M_2)q] \quad \text{[Equation 1]}$$

$$[L(M_1M_2M_2M_1)q] \quad \text{[Equation 2]}$$

Herein, $M_1$ is the first segment, $M_2$ is the second segment, q is the number of times of the repetition of the first and second segments, and L is the lengths of the first and second segments.

In particular, L may be an integer between 10 and 500, 10 and 100, 30 and 75, or 150 and 500, $M_1$ and $M_2$ may represent independent numbers, and q may be an integer between 1 and 10, 2 and 10, or 1 and 2.

For example, in the nanobarcode, Equations 1 and 2 may be represented by any one of $[30(M_1M_2)_{10}]$, $[75(M_1M_2)_4]$, $[75(M_1M_2M_2M_1)_2]$, $[150(M_1M_2)_2]$, $[150(M_1M_2M_2M_1)_1]$, and $[300(M_1M_2)_1]$. In this case, $M_1$ means the first segment and $M_2$ means the second segment. In particular, the nanobarcode may be provided in a rod shape satisfying any one of $[30(01)_{10}]$, $[75(01)_4]$, $[75(0110)_2]$, $[150(01)_2]$, $[150(0110)_1]$, and $[300(01)_1]$.

The nanobarcode satisfying Equation 1 may tune the periodicity of the ligand peptide bound to the second segment by controlling the lengths L of the first and second segments. The nanobarcode satisfying Equation 2 may tune any one or more of the periodicity and a sequence of the ligand peptide bound to the second segment compared to the nanobarcode satisfying Equation 1.

The first segment may have a structure in which a carboxylate is substituted. The carboxylate substituent may be an amino acid derivative, particularly aminocaproic acid. The first segment has the structure in which a carboxylate is substituted, thereby improving coupling force with the substrate and exhibiting excellent durability.

The integrin ligand peptide bound to the second segment may include a thiolated integrin ligand peptide, and may have a structure in which a thiol group of the integrin ligand peptide is chemically bound to the second segment. It is possible to efficiently control adhesion and polarization of the macrophage by tuning the periodicity and sequences of the ligand peptide by binding the integrin ligand peptide to the second segment.

Figure 2:
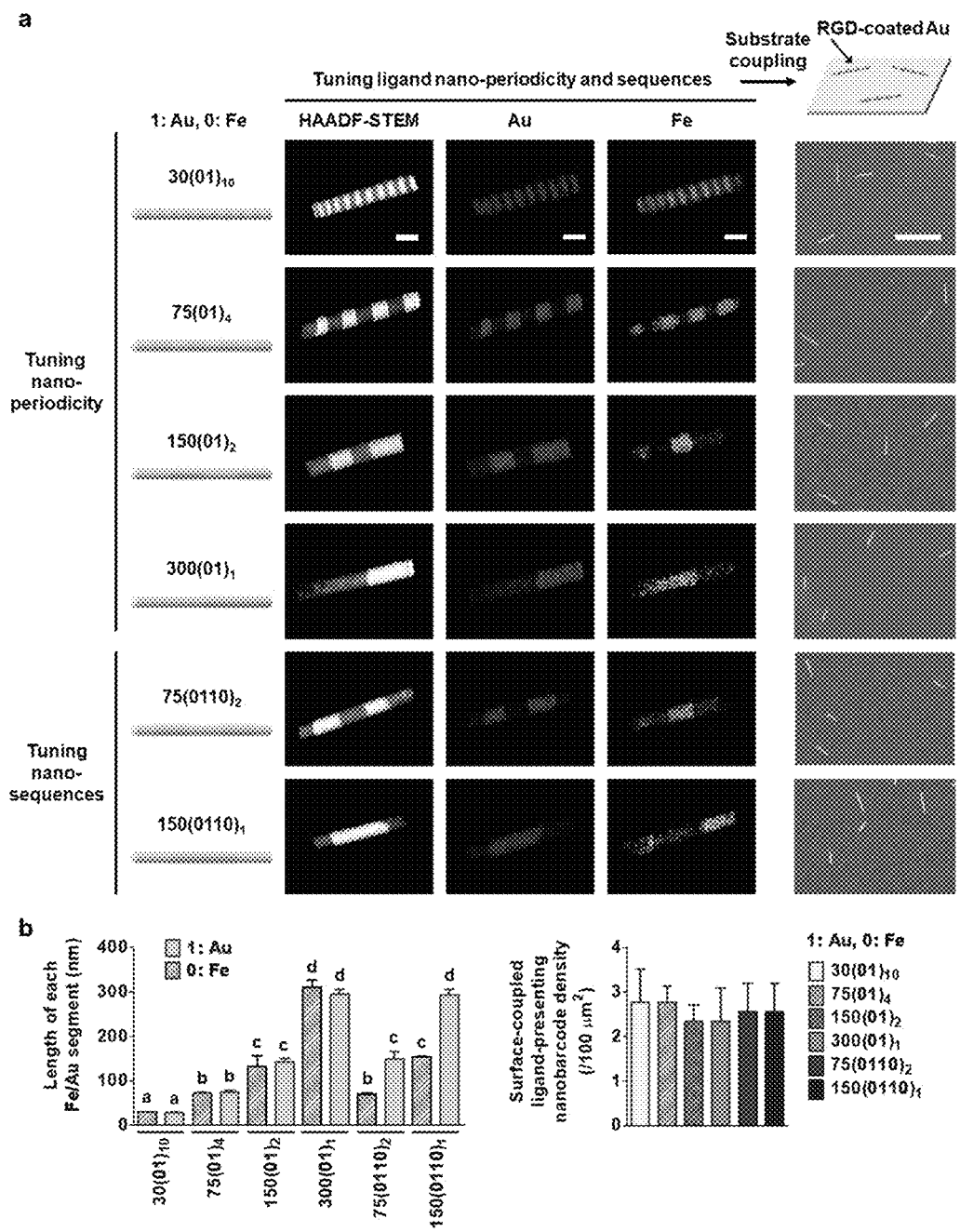
FIG. 2 is a High-angle annular dark field scanning transmission electron microscopy (HAADF-STEM) image, and energy dispersive spectroscopy (EDS) mapping and field emission scanning electron microscopy (FE-SEM) image of a nanobarcode according to the exemplary embodiment of the present invention.

Further, a of FIG. 2 is high-angle annular dark field scanning transmission electron microscopy images and field emission scanning electron microscopy images of the nanobarcode for controlling adhesion and polarization of the microphages according to the present invention, and it can show a size of the nanobarcode. In particular, the nanobarcode has a rod shape with a circular cross section and may have a diameter of 50 nm to 100 nm. More particularly, the nanobarcode may have a diameter of 60 nm to 90 nm, or 50 nm to 80 nm. Further, the nanobarcode may have a rod shape having a length of 200 nm to 1,000 nm. When the length of the nanobarcode is less than 200 nm, binding efficiency of the integrin ligand may deteriorate, and when the length of the nanobarcode is larger than 1000 nm, the degree of distribution may deteriorate when nanobarcode is bound onto the substrate. More particularly, the nanobarcode may have a length of 500 nm to 800 nm, or 600 nm to 900 nm. The present invention includes the nanobarcode, thereby controlling the adhesion and polarization of the macrophage according to the structure of the nanobarcode.

Further, the present invention provides a method of preparing the nanobarcode for controlling adhesion and polarization of macrophages, the method including: preparing a nanobarcode in which a first segment containing iron (Fe) and a segment containing gold (Au) are repeatedly formed; substituting a carboxylate substituent on the first segment by mixing the nanobarcode and a first suspension; and mixing the nanobarcode and a second suspension including the integrin ligand peptide (RGD).

The operation of preparing the nanobarcode may include an electroplating process and a process of etching an anodized nanotemplate in which iron and gold are alternately into pores of the nanotemplate by using a first current and a second current lower than the first current, respectively, by using the anodized nanoframe to form an iron-gold multi-layered nanowires.

As the nanotemplate, an anodic aluminum oxide (AAO) nanotemplate, an inorganic nanotemplate, or a polymer nanotemplate is used. Herein, the case which utilizes the AAO nanotemplate is illustrated. A diameter of the nanowire is determined according to a diameter of a pore of the AAO nanotemplate, and a length of the nanowire is determined according to a growth rate and duration time of each segment.

The used AAO nanotemplate includes the plurality of pores, of which a diameter has 200 nm.

A silver (Ag) electrode layer having a thickness of 250 nm is formed on the bottom surface of the AAO nanotemplate by an electron beam evaporation method before electroplating. The electrode layer serves as a cathode during electroplating. Herein, as the electrode layer, other metals or other conductive material layers may be used.

Fe/Au barcode nanowires are synthesized inside the AAO nanotemplate pores by a pulse plating method in which a voltage or a current is alternately applied so that an Fe layer is synthesized at a high voltage or current and an Au layer is synthesized at a low voltage or current.

A precursor solution for electroplating is prepared in which iron (II) sulfate heptahydrate ($FeSO_4$ $7H_2O$ 278.02 g/mol) and potassium dicyanoaurate(I) ($KAu(CN)_2$ 288.10 g/mol) are adjusted to have a certain ratio of mole concentration, in one plating bath. To maintain stable and mild environment during electroplating, boric acid ($H_3BO_3$) is added as a buffer solution.

Herein, since it is necessary to put two kinds of precursors into one plating bath and synthesize a nanowire containing two different elements, two kinds of precursors should not react and form a product when the precursors are selected.

Further, each element needs to be separated in the multilayer structure through modulating a ratio of the ionic content of the element with higher reduction potential to the content of the element with lower reduction potential. The ratio of the molar concentration of iron to gold ions in the used solution ranges 40:1 to 4:1 (preferably, 16:1), and the nanowire in which two kinds of elements form each layer respectively may be synthesized by adding a relatively low concentration of gold that is a noble metal.

The electrolyte is prepared by using deionized water, and the hydrogen ionization concentration (pH value) is kept constant by using boric acid ($H_3BO_3$) to maintain the stable and mild environment during electroplating.

The Fe/Au multilayer structure barcode-type nanowire is formed by performing pulse electroplating on the anotemplate. The current of 10 $mA/cm^2$ was applied for electroplating the iron irons and the current of 1.0 $mA/cm^2$ was applied for electroplating the gold irons.

The iron and the gold have different standard reduction potentials, and by using the difference in the reduction potential, iron may be plated at a relatively high current, and gold may be plated at a relatively low current as described above. Therefore, it is possible to manufacture an Fe/Au multilayer thin film nanowire.

Next, to obtain an individual multilayer thin film nanowire, when the anodized nanotemplate is treated with a 1M sodium hydroxide (NaOH) solution at a room temperature for one hour, both the nanotemplate and the electrode layer are melted and the barcode-type iron/gold (Fe/Au) multilayer thin film nanowire may be separated.

The diameter of the nanowire may be controlled by using the anodized aluminum nanotemplate having different pore sizes, and a thickness of each layer of the iron and the gold of the nanowire may be controlled by changing the electroplating time.

Further, the operation of substituting the carboxylate substituent on the first segment may be performed by mixing the nanobarcode and the first suspension and reacting the nanobarcode and the first suspension for 8 to 20 hours to 10 to 15 hours. The first suspension may contain an amino acid derivative containing a carboxylate substituent, and specifically, the amino acid derivative may be aminocaproic acid. The carboxylate substituent is substituted in the oxide layer of the iron segment by reacting the nanobarcode with the first suspension as described above, so that the coupling to the substrate may be facilitated.

Further, the operation of mixing the nanobarcode and the second suspension may be performed by stirring the nanobarcode in the second suspension including the integrin ligand peptide (RGD) for 1 to 5 hours or 1 to 3 hours. In this case, the thiolated RGD peptide ligand may be bound to the second segment of the nanobarcode. The solvent may contain any one or more of dimethylformaldehyde (DMF) and dimethyl sulfoxide (DMSO). The integrin ligand peptide is bound to the second segment to tune periodicity and sequence of the ligand of the nanobarcode. Accordingly, it is possible to easily control the adhesion and phenotype of the macrophage by using the nanobarcode.

Further, the present invention provides a method of controlling adhesion and polarization of macrophages, the method including: manufacturing a nanobarcode-presenting substrate by putting a substrate of which a surface is activated in a solution containing the nanobarcode for controlling adhesion and polarization of the macrophage; and controlling adhesion and polarization of the macrophage after treating the nanobarcode-presenting substrate with a culture medium.

b of FIG. 1 is a diagram schematically illustrating the method of controlling adhesion and polarization of the macrophage according to the exemplary embodiment of the present invention. Referring to b of FIG. 1, it can be seen that the adhesion of the macrophage is promoted by tuning periodicity and sequences of the integrin ligand peptide bound to the second segment of the nanobarcode, and the substrate is activated by adjusting inflammatory M1 phenotype and regenerative M2 phenotype.

In particular, the operation of manufacturing the nanobarcode-presenting substrate may include: soaking the surface of the substrate in an acidic solution; and activating the surface of the substrate by putting the soaking—completed substrate in an aminosilane solution.

In the operation of soaking the surface of the substrate in the acidic solution, the surface of the substrate may be soaked in the acidic solution including any one or more of hydrochloric acid and sulfuric acid for 30 minutes to 2 hours or 30 minutes to 1 hour. Accordingly, by binding a hydroxyl group to the surface of the substrate, the activation of the surface of the substrate may be effectively performed so that it is easy to bond with an amino group of the aminosilane solution.

In the operation of activating the surface of the substrate, the surface of the substrate may be activated by putting the substrate in the amino-silane solution. The amino-silane solution may include (3-aminopropyl)triephoxysilane (APTES). In this case, the activation of the surface of the substrate means that the surface of the substrate is positively charged, and particularly, the surface of the substrate may be activated by binding an amine group onto the substrate. The surface of the substrate is positively charged by activating the surface of the substrate by soaking the substrate in the amino-silane solution, so that the substrate may be chemically bound to the iron segment of the nanobarcode.

For example, the nanobarcode-presenting substrate may be the substrate obtained by inactivating the surface of the substrate which is not coupled with the nanobarcode by putting the substrate in a solution containing a polyethylene glycol derivative.

The operation of controlling adhesion and polarization of the macrophage may be performed by changing any one or more of periodicity and sequences of the ligand bound to the nanobarcode of the nanobarcode-presenting substrate.

In particular, in the operation of controlling adhesion and polarization of the macrophage, in the case where the substrate including the rod-type nanobarcode satisfying Equation 1 below is used, the inflammatory (M1) phenotype may predominate.

$$[L(M_1M_2)q] \qquad \text{[Equation 1]}$$

Herein, $M_1$ is the first segment, $M_2$ is the second segment, q is the number of times of the repetition of the first and second segments, q is an integer between 2 and 10, and L is lengths of the first and second segments.

Further, in the operation of controlling adhesion and polarization of the macrophage, in the case where the substrate including the rod-type nanobarcode satisfying Equation 2 below is used, the regenerative and inflammatory (M2) phenotype may predominate.

$$[L(M_1M_2M_2M_1)q] \qquad \text{[Equation 2]}$$

Herein, $M_1$ is the first segment, $M_2$ is the second segment, q is the number of times of the repetition of the first and second segments, q is an integer between 1 and 5, and L is lengths of the first and second segments.

More particularly, in Equation 1, L may be an integer between 10 and 100 or 30 to 75. Further, in Equation 2, L may be an integer between 150 and 500 or 150 and 300, and q may be an integer of between 1 and 2.

For example, in the nanobarcode, Equations 1 and 2 may be represented by any one of $[30(M_1M_2)_{10}]$, $[75(M_1M_2)_4]$, $[75(M_1M_2M_2M_1)_2]$, $[150(M_1M_2)_2]$, $[150(M_1M_2M_2M_1)_1]$, and $[300(M_1M_2)_1]$. In this case, $M_1$ means the first segment and M2 means the second segment. In particular, the nanobarcode may be provided in a rod shape satisfying any one of $[30(01)_{10}]$, $[75(01)_4]$, $[75(0110)_2]$, $[150(01)_2]$, $[150(0110)_1]$, and $[300(01)_1]$.

It is possible to effectively control adhesion and phenotype of the macrophage by tuning periodicity and sequences of the integrin ligand peptide on the nanobarcode by binding the integrin ligand peptide to the second segment of the nanobarcode having the foregoing structural formula.

Hereinafter, examples of the present invention will be described. However, the examples below are merely preferable examples of the present invention, and the scope of the present invention is not limited by the examples.

PREPARATION EXAMPLE

Preparation Examples 1 to 6

Prepare Nanobarcode

An Fe/Au nanobarcode was prepared to represent various ligand nano-periodicity and ligand sequences on a substrate. As a mold of a pulse electrodeposition process, a porous polycarbonate membrane (PCM) with a pore diameter of 70 nm was used. Silver (Ag) was deposited in the pores of the porous PCM by using an electron beam evaporator. To fill the pores of the PCM with the nanobarcode, a precursor solution was prepared with 0.06 M iron sulfate heptahydrate ($FeSO_4 7H_2O$), 0.01 M potassium dicyanoaurate ($KAu(CN)_2$), and 0.6 M boric acid ($H_3BO_3$). After the pores of the porous PCM are filled with the precursor solution, a pulse current was applied to induce an electrochemical reaction while using a platinum (Pt) plate as a counter electrode.

Due to the significantly different reduction potentials of Fe and Au, Fe and Au were separately deposited in a predetermined order in response to applied pulse currents which are composed of distinctly different current densities. Lengths of the Fe and Au segments were controlled by modulating a pulse duration time.

Six periodically sequenced Fe/Au nanobarcodes with tunable nano-periodicity and the sequence which does not modulate the sizes of the total Fe and Au segments were precisely prepared by optimizing pulse current density and duration time. Four periodically sequenced Fe/Au nanobarcodes were prepared so as to represent tunable Fe and Au nano-periodicity having the same nano-sequence Nanobarcode [30(01)$_{10}$] (Preparation Example 1) formed of 30 nm-long Fe and Au segments with 10 repeated sequences was prepared by alternately applying 4 mA/cm$^2$ for 0.7 second and 0.25 mA/cm$^2$ for 9 seconds, respectively. The naming regulation of the structure of the nanobarcode is as follows. The Au and Fe segments were designated as 1 and 0, respectively. In the nanobarcode [30(01)$_{10}$], the length (nm) of each segment was designated as 30, but the repeated sequence of each segment was designated as 10. Nanobarcode [75(01)$_4$] (Preparation Example 2) formed of 75 nm-long Fe and Au segments with four repeated sequences was prepared by alternately applying 4 mA/cm$^2$ for 1.7 seconds and 0.25 mA/cm$^2$ for 22 seconds, respectively. Nanobarcode [150(01)$_2$] (Preparation Example 3) formed of 150 nm-long Fe and Au segment with two repeated sequences was prepared by alternately applying 4 mA/cm$^2$ for 3.6 seconds and 0.25 mA/cm$^2$ for 45 seconds, respectively. Nanobarcodes formed of 300 nm-long Fe/Au segment [300(01)$_1$] (Preparation Example 4) were prepared by alternately applying 4 mA/cm$^2$ for 7.2 seconds and 0.25 mA/cm$^2$ for 90 seconds, respectively.

To tune nano-periodicity and sequences, two periodically sequenced Fe/Au nanobarcodes were prepared. Nanobarcode [75(0110)$_2$] (Preparation Example 5) formed of a 75-nm-long Fe segment, a 150 nm-long Au segment, and a 75 nm-long Fe segment with two repeated sequences were prepared by alternately applying 4 mA/cm$^2$ for 1.7 seconds, 0.25 mA/cm$^2$ for 44 seconds, and 4 mA/cm$^2$ for 1.7 seconds, respectively. Nanobarcode [150(0110)$_1$] (Preparation Example 6) formed of a 150 nm-long Fe segment, a 300 nm-long Au segment, and a 150 nm-long Fe segment was prepared by alternately applying 4 mA/cm$^2$ for 3.6 seconds, 0.25 mA/cm$^2$ for 90 seconds, and 4 mA/cm$^2$ for 3.6 seconds. Six periodically sequenced Fe/Au nanobarcodes and sequences with tunable nano-periodicity were obtained by physically separating an Ag layer from the porous PCM and chemically removing the porous PCM for 1.5 hours and 0.5 hour with dichloromethane and chloroform, respectively. Subsequently, the nanobarcode was washed three times with acetone and ethanol, and was dispersed in 1 mL of deionized water (DI) before functionalization for substrate coupling.

Comparative Preparation Example 1

A nanobarcode was prepared by the same method as that of Preparation Example 1 except that a negatively charged thiolated RGD peptide (CDDRGD, GL Biochem) was not added.

EXAMPLE

Examples 1 to 6

Manufacture Nanobarcode-Presenting Substrate

The six periodically sequenced nanobarcodes prepared in Preparation Examples 1 to 6 were chemically functionalized and grafted to a substrate to express various nano-periodicity of ligand sequences. Since it is well known that the amine group may be coupled to a natural oxide layer, the amine group of aminocaproic acid was used to be coupled to the natural oxide layer of the iron (Fe) segment in the nanobarcode to represent the carboxylate group after surface functionalization. A mixed solution of 1 mL of nanobarcode and 1 mL of 6 mM aminocapronic acid solution was stirred at a room temperature for 12 hours, and then centrifuged and washed with deionized water. A 22 mm×22 mm flat cell culture grade glass substrate was aminated to allow the carboxylate groups on the surfaces of the six different nanobarcodes to bind to the amine groups on the substrate. The substrate was first washed with a mixture in which hydrochloric acid and methanol were mixed at a ratio of 1:1 and rinsed with deionized water. The substrate was soaked in sulfuric acid for 1 hour to activate the hydroxyl group and rinsed with deionized water. The substrate was aminated for 1 hour in 3-aminopropyl triethoxy silane (APTES) and ethanol (1:1) in a darkroom and washed with ethanol, followed by drying for 1 hour at 100° C. The aminocaproic acid-bound six periodically sequenced nanobarcodes in 1 mL of deionized water were activated through the EDC/NHS reaction for 3 hours in 0.5 mL of 20 mM N-ethyl-N'-(3-(dimethylaminopropyl) carbodiimide) (EDC) and 0.5 mL of 20 mM N-hydroxysuccinimide (NHS), and then washed with deionized water.

The six periodically sequenced nanobarcodes were coupled to the aminated substrate to present the tunable ligand nano-periodicity and sequences by precisely optimizing nanobarcode concentration (1 to 2 mL) and reaction time (2 to 3 h) in the six periodically sequenced nanobarcodes with maintaining constant the substrate-coupled nanobarcode and the ligand density. The thiolated RGD peptide ligand was grafted to the Au segments in the nanobarcode-coupled substrate. The nanobarcode-coupled substrate was cultured for 2 hours by using 0.2 mM thiolated RGD peptide ligand (GCGYCFCDSPG, GLBiochem) in dimethylsulfoxide (DMSO) with 0.25% N,N-diisopropylethylamine (DIPEA) and 10 mM tris(2-carboxyethyl)phosphine hydrochloride (TCEP), and then washed with deionized water. Non-RGD ligand-specific macrophage adhesion was minimized by blocking the non-nanobarcode-coated areas on the substrate with 100 mM-methoxy-poly(ethylene glycol)-succinimidyl carboxymethyl ester with 0.2% N,N-diisoprophylethylamine (DIPEA) in deionized water for 2 hours in the dark condition and then washed with deionized water.

Comparative Example 1

A nanobarcode-presenting substrate was manufactured with the same method except that the nanobarcode prepared in Comparative Example 1 was used.

EXPERIMENTAL EXAMPLE

Experimental Example 1

Figure 6:
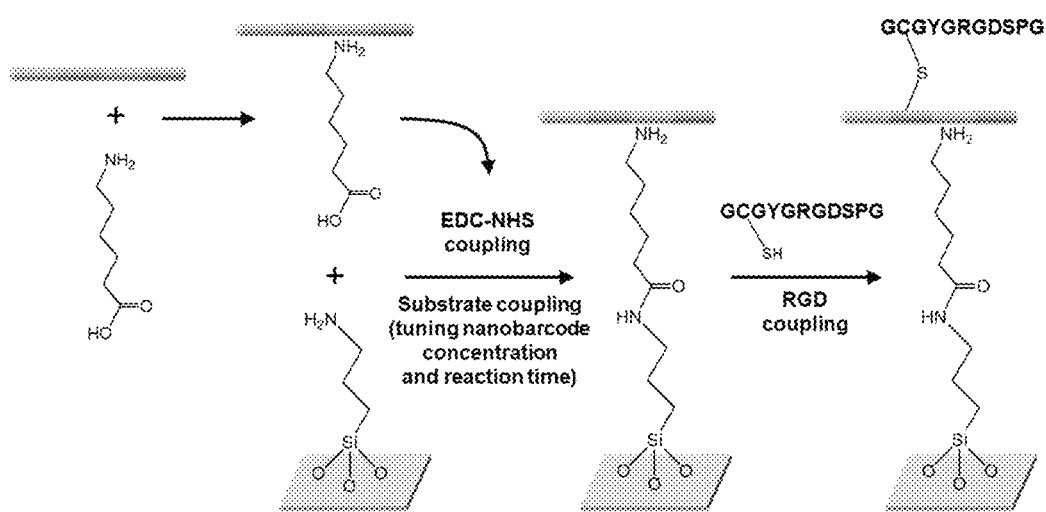
FIG. 6 is an image schematically illustrating operations for manufacturing a substrate including the nanobarcode according to the exemplary embodiment of the present invention.

To check the form and the chemical characteristic of the nanobarcode according to the present invention, high-angle annular dark field scanning transmission electron microscopy (HAADF-STEM) analysis, energy dispersive spectroscopy (EDS) analysis, X-ray diffraction (XRD) analysis, vibrating sample magnetometry (VSM), and Fourier transform infrared spectroscopy (FT-IR) analysis were performed on the prepared nanobarcode, and the result thereof is represented in FIGS. 2 and 6.

In particular, to characterize the sizes and the shapes of the six periodically sequenced Fe/Au nanobarcodes with tunable nano-periodicity and sequences, the HAADF-STEM imaging was performed according to the previously demonstrated procedure. The HAADF-STEM imaging was conducted at 200 kV by using a probe Cs-corrected JEM ARM200CF (JEOL Ltd.) under spherical aberration (C3) of 0.5 to 1.0 μm resulting in a phase of 27 to 28 mrad. The convergence semi-angle for imaging was 21 mrad whereas the collection semi-angle for HAADF was 90-370 mrad. Micrographs were acquired at electron probe sizes of 8C & 9C (JEOL defined), which were measured to be 1.28 and 1.2 Å, respectively, and a pixel dwell time of 10-15 μs with 2048×2048 pixel area. When an emission current of 8-13 μA is used, a probe current range of 10-20 Pa is calculated. A 40 μm aperture was used, which yielded a beam convergence semi-angle of α=27.5 mrad. The electron dose introduced per image varied in around 1,000-2,000 e/Å 2 depending on the magnification. In the obtained image, darker and brighter shapes represent Fe and Au segments, respectively. The nanoscale dimensions (length, diameter, and surface area) of each or total Fe and Au segments with sharp interfaces in the nanobarcode were calculated by using HADDF-STEM imaging. Through the calculation, it was confirmed that the six periodically sequenced Fe/Au nanobarcodes with tunable nano-periodicity and sequences have the similar dimensions of the total Fe and Au segments. The Fe and Au segments with sharp interfaces in the six periodically sequenced Fe/Au nanobarcodes were specifically identified through EDS mapping using two SOD detectors (Thermo Fisher Scientific). The Fe and Au element mapping was individually used for identifying the Fe and Au segment in the six periodically sequenced Fe/Au nanobarcodes with tunable nano-periodicity and sequences obtained by strictly individually modulating a pulse, a current segment, and a duration time.

The co-existence of Fe and Au segments repeated in the six periodically sequenced nanobarcodes was confirmed by carrying out the X-ray diffraction analysis (D/MAX-2500V/PC, Rigaku). The peaks were assigned with crystalline indices of the Fe and Au phases present in the six periodically sequenced nanobarcodes by using Powder Diffraction File (PDF) data of the Fe phase (PDF #870722) and the Au phase (PDF #040784).

The magnetic properties of the Fe segments in the six periodically sequenced nanobarcodes were analyzed through vibrating sample magnetometry(VSM) measurement under an applied magnetic field (H) at a room temperature. The corresponding magnetic moment (M) is indicated with hysteresis loops after normalization to the maximum value of the magnetic moment in each nanobarcode.

FIG. 2 is high-angle annular dark field scanning transmission electron microscopy (HAADF-STEM) image, and energy dispersive spectroscopy (EDS) mapping and field emission scanning electron microscopy (FE-SEM) image of a nanobarcode according to the exemplary embodiment of the present invention. Referring to FIG. 2, the Fe and Au segments alternating in the HAADF-STEM image were identified with dark and bright contrast areas, and it was confirmed that the Fe and Au segments have the sharp interfaces without alloy formation through the EDS mapping image for each Fe and Au element.

Referring to b of FIG. 2, the nano sizes (length, diameter, and surface area) of each or total Fe and Au segments were accurately quantified in the nanobarcode. In particular, the length of each Fe/Au segment in the nanobarcode was represented with 30.8±0.3 nm/28.1±1.8 nm in $[30(01)_{10}]$ group, 72.3±1.4 nm/74.6±4.3 nm in $[75(01)_4]$ group, 132.7±19.2 nm/142.5±6.1 nm in $[150(01)_2]$ group, 310.7±13.0 nm/294.7±9.5 nm in $[300(01)_1]$ group, 69.3±3.0 nm/149.7±13.7 nm in $[75(0110)_2]$ group, and 154.2±1.3 nm/302.1±3.6 nm in $[150(0110)_1]$ group. Through this, it was seen that the nano-periodicity and sequences were systematically turned in the six different nanobarcodes by precisely regulating pulse current density and duration while the nano-periodicity and sequences were synthesized.

Figure 3:
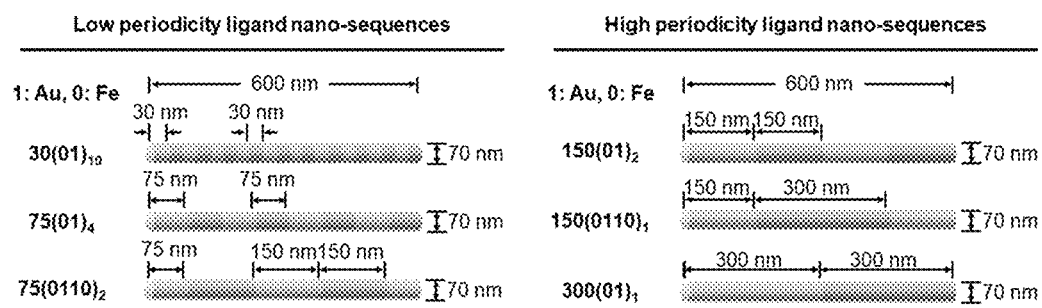
FIG. 3 is a schematic diagram (a) of the nanobarcode according to the exemplary embodiment of the present invention, and graphs illustrating a total length (b), a diameter (c), and a surface area (d) of each of Fe and Au (Fe/Au) nanobarcodes calculated from the result of the HAADF-STEM.
Figure 3:
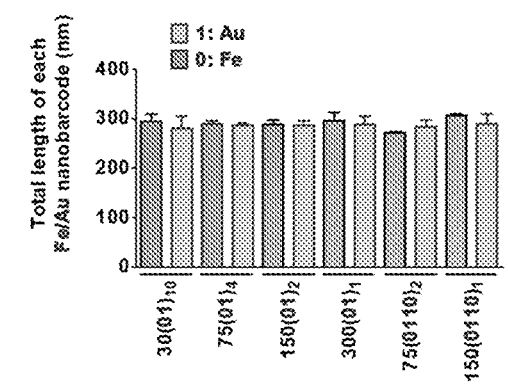
Figure 3:
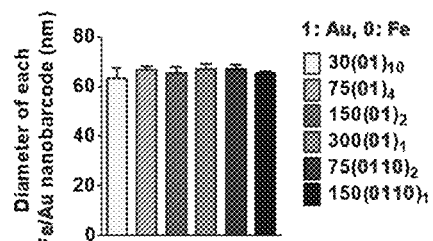
Figure 3:
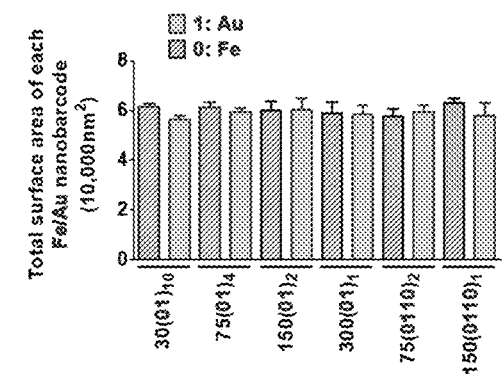

FIG. 3 is a schematic diagram (a) of the nanobarcode prepared in the present invention, and graphs illustrating a total length (b), a diameter (c), and a surface area (d) of each of Fe and Au nanobarcodes calculated from the result of the HAADF-STEM. Referring to FIG. 3, in contrast, total lengths of Fe vs. Au segment in each nanobarcode ranged from 270.7 to 306.2 nm vs. from 279.9 to 289.1 nm, respectively, in the six different nanobarcodes without significant differences. The diameters of each Fe/Au nanobarcode ranged from 63.2 to 66.9 nm in the six different nanobarcodes without significant differences. The total surface area of the Fe vs. Au segment in each nanobarcode ranged from 57500 to 61420 $nm^2$ vs. from 56270 to 60330 $nm^2$, respectively, in the six different nanobarcodes without significant differences. These results collectively indicate that the six periodically sequenced Fe/Au nanobarcodes were precisely prepared to display the tunable ligand nano-periodicity and sequences without modulating the dimensions of total Fe and Au segments. In this case, Au and Fe segments were referred to as 1 and 0 in parentheses, respectively, and the length (nm) of each Au and Fe segment was referred to as 30, 75, 150, and 300.

Figure 4:
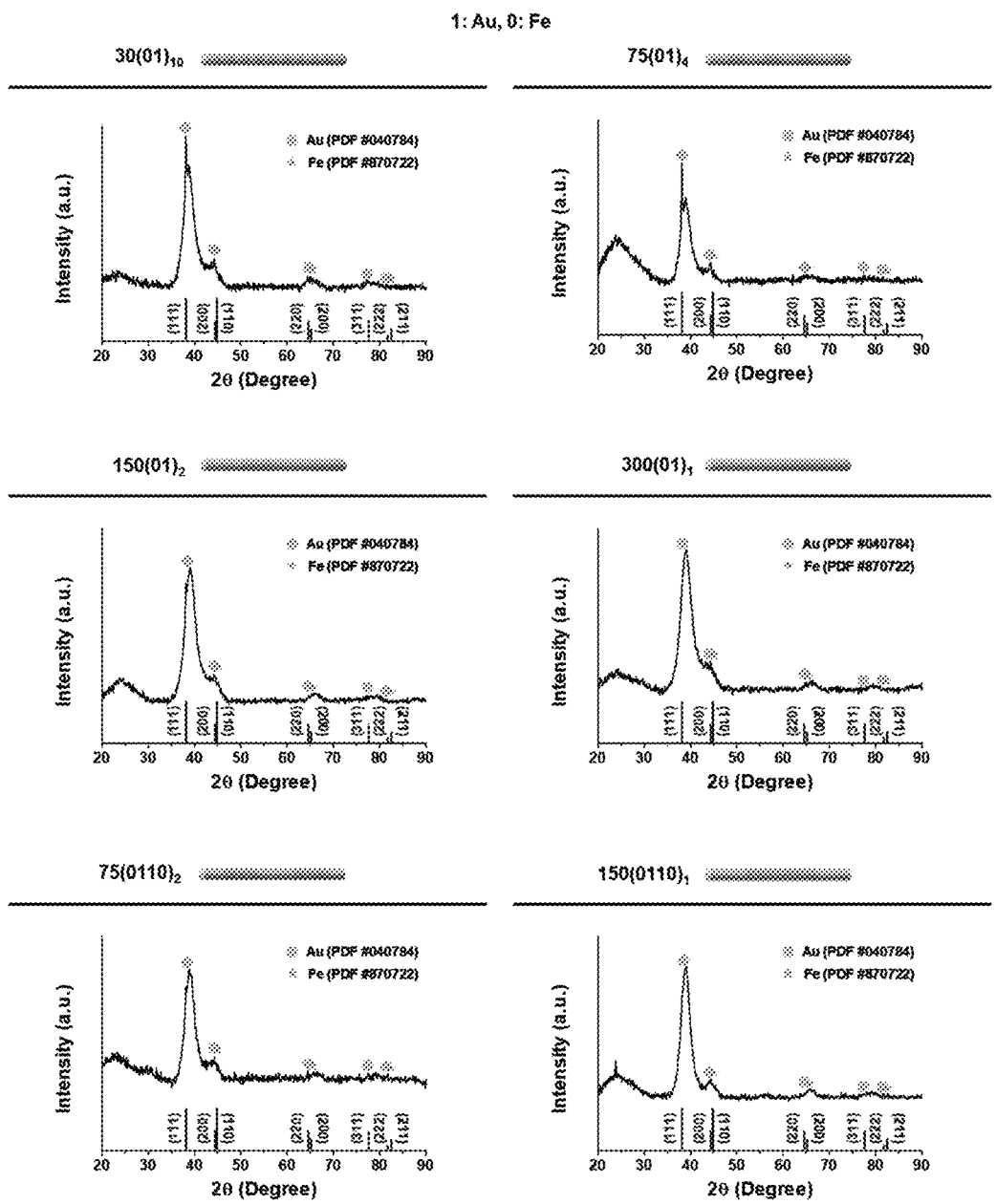
FIG. 4 is an X-ray diffraction analysis graph of the nanobarcode according to the exemplary embodiment of the present invention.

FIG. 4 is an X-ray diffraction analysis graph of a nanobarcode according to the exemplary embodiment of the present invention. Referring to FIG. 4, the crystalline phases of the Fe and Au segments in nanobarcodes were analyzed via X-ray diffraction, which revealed that diffraction peaks corresponding to the Fe and Au phases were similarly co-present in the six different nanobarcodes. Through this, it can be seen that the six periodically sequenced Fe/Au nanobarcodes exhibit the similar property.

Figure 5:
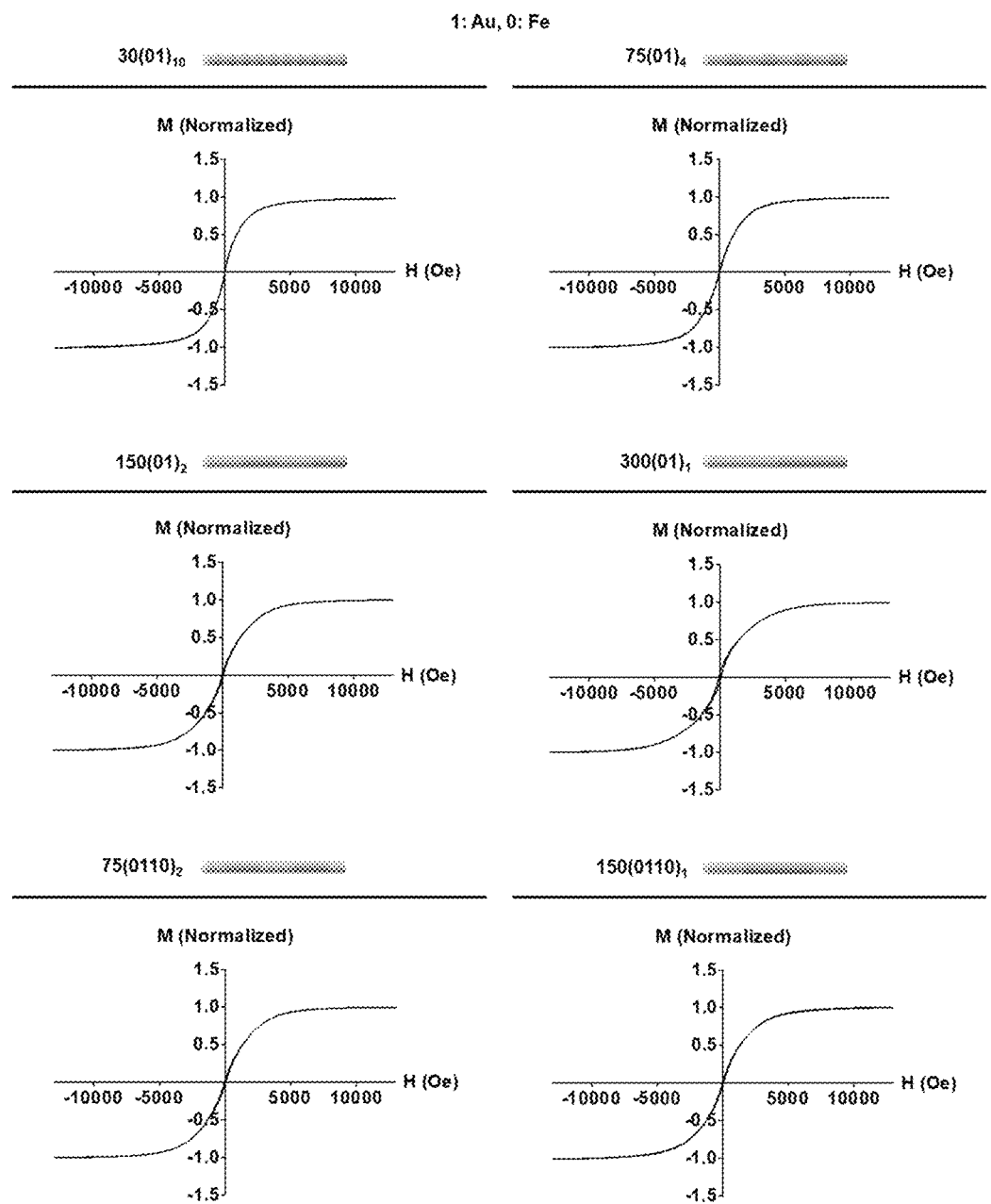
FIG. 5 is a graph illustrating a measurement result of a vibrating sample magnetometry (VSM) of the nanobarcode according to the exemplary embodiment of the present invention.

FIG. 5 is a graph illustrating a measurement result of the VSM of the nanobarcode according to the exemplary embodiment of the present invention. In particular, the magnetic properties of nanobarcodes due to the presence of the Fe segments were analyzed revealing that all of six different nanobarcodes exhibit similar magnetic behaviors without obvious hysteresis. This magnetic property may be utilized for the reversible remote control of the nanobarcodes of the present invention by using an external magnetic field.

Experimental Example 2

Figure 7:
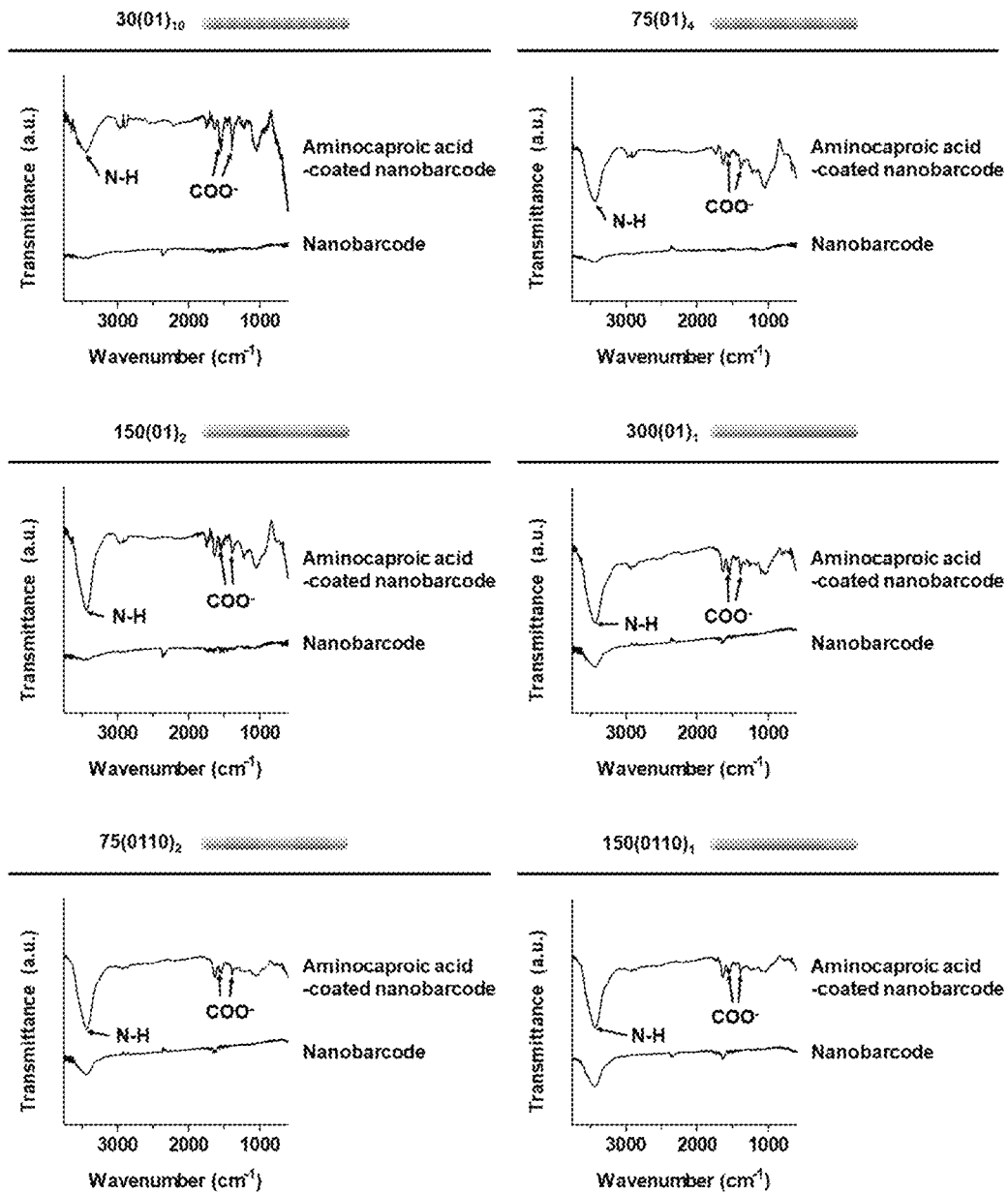
FIG. 7 is a diagram illustrating a result of a Fourier transform infrared spectroscopy (FT-IR) analysis of the nanobarcode according to the exemplary embodiment of the present invention.

To check the property of the substrate including the nanobarcode according to the present invention, the substrate including the nanobarcode was photographed with the FE-SEM and the FT-IR was carried, and the results thereof are represented in FIGS. 2 and 7.

The FT-IR was conducted by using GX1 (Perkin Elmer Spectrum, USA) to confirm the chemical bond characteristics of the nanobarcode. The samples subjected to the analysis of changes in chemical bond characteristics were lyophilized and densely packed into KBr pellet prior to the analysis.

FIG. 6 is an image schematically illustrating operations for manufacturing a substrate including the nanobarcode according to the exemplary embodiment of the present invention. Referring to FIG. 6, the six periodically sequenced nanobarcodes was chemically functionalized before being grafted to the substrate. The amine group of aminocaproic acid was coupled to a natural oxide layer of the Fe segment of the nanobarcode to display a carboxylate group. Various ligand nano-periodicities and sequences were confirmed without modulating the nanobarcode coupled to the substrate and the ligand density by precisely optimizing a concentration and reaction time of the nanobarcode by activating the carboxylate group in the aminocaproic acid-coated nanobarcode and grafting the nanobarcode onto the aminated substrate. Subsequently, thiolated RGD ligands were grafted to Au segments in the nanobarcode-coupled substrate. The density of the substrate-coupled ligand-presenting nanobarcode, as well as the dimensions of the total Fe and Au segments, are similarly maintained, to separate the effect of ligand density for the substrate. Referring to FIG. 2, the substrate-coupled ligand-presenting nanobarcodes were visualized by using field emission scanning electron microscopy, which revealed their uniform distribution in a monolayer. Their densities ranged from 0.0235 to 0.0277 per $\mu m^2$, thereby confirming the successful maintenance of a similar density in all of the substrate-coupled ligand-presenting nanobarcodes without significant differences. Through the following experiment, it was confirmed that the density may efficiently control the adhesion and phenotypic polarization of macrophages.

FIG. 7 is a diagram illustrating a result of a Fourier transform infrared spectroscopy (FT-IR) analysis of the nanobarcode according to the present invention. Referring to FIG. 7, it can be seen the chemical bond characteristics of the aminocaproic acid-coated nanobarcodes. In particular, COO bonds were revealed at 1560 to 1565 $cm^{-1}$ and 1387 to 1389 $cm^{-1}$ and N—H bonds were revealed at 3432 to 3448 $cm^{-1}$. Through this, it is confirmed that the aminocaproic acid was successfully coupled to the six different nanobarcodes.

Experimental Example 3

Figure 8:
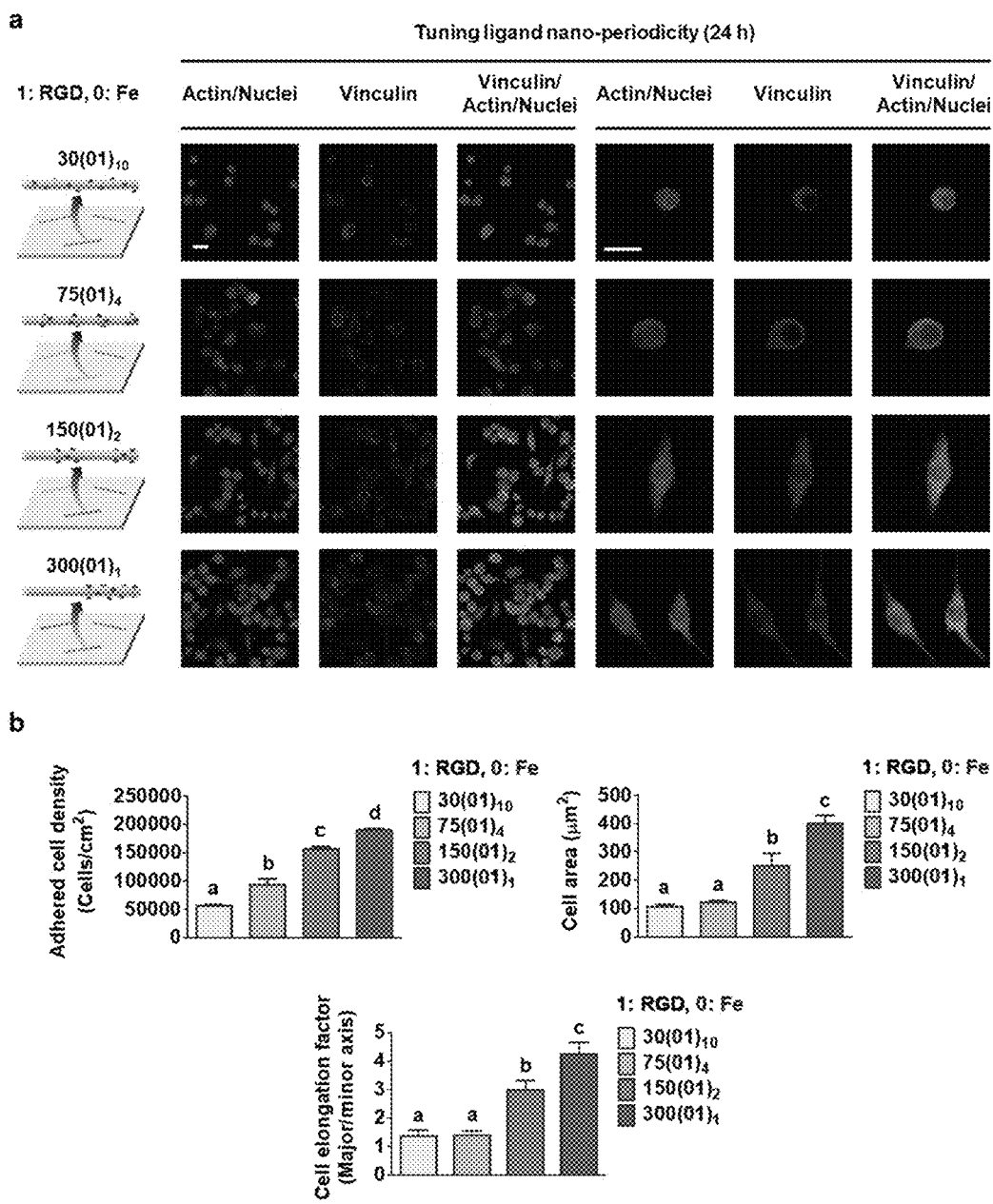
FIG. 8 is an immunofluorescent confocal image of macrophages (after 24 hours) cultured by using the nanobarcode according to the exemplary embodiment of the present invention against F-actin, nucleus, and vinculin, and in this case, a scale bar represents 20 μm.
Figure 9:
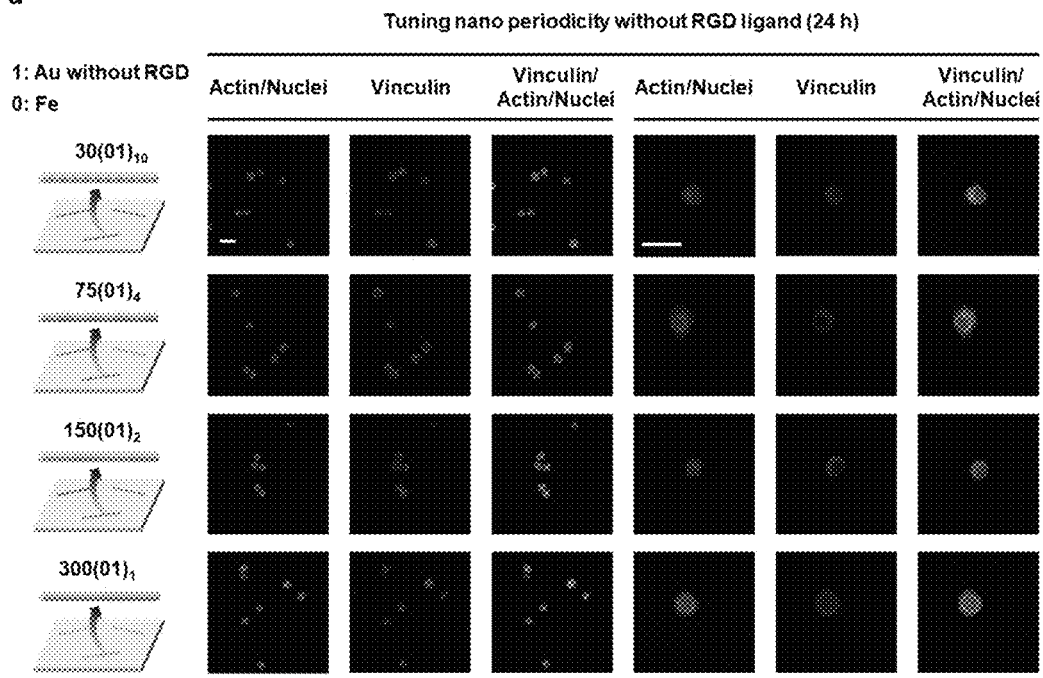
FIG. 9 is a result of an adhesion experiment of macrophages by tuning nano-periodicity in a nanobarcode (in the case where there is no RGD ligand binding) according to a Comparative Example of the present invention.
Figure 9:
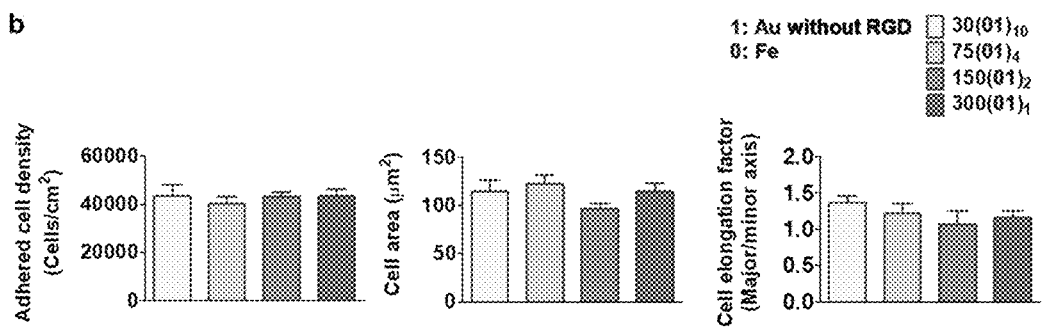
Figure 10:
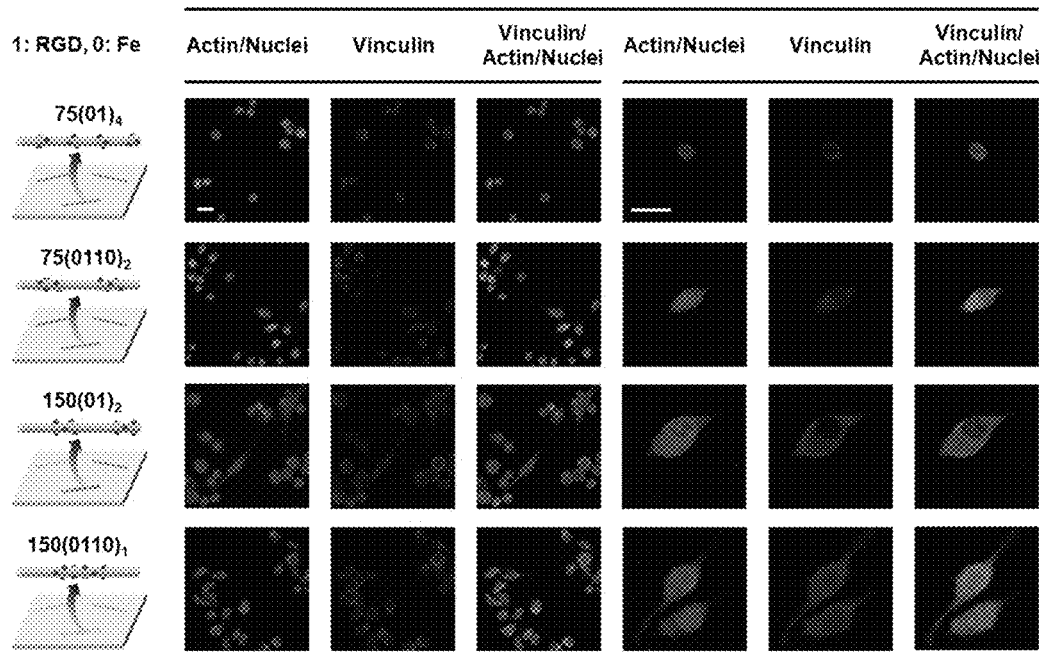
FIG. 10 is an immunofluorescent confocal image of macrophages (after 24 hours) cultured by using the nanobarcode (in which nano-periodicity and ligand sequences are tuned) according to the exemplary embodiment of the present invention against F-actin, nucleus, and vinculin, and in this case, a scale bar represents 20 μm.
Figure 10:
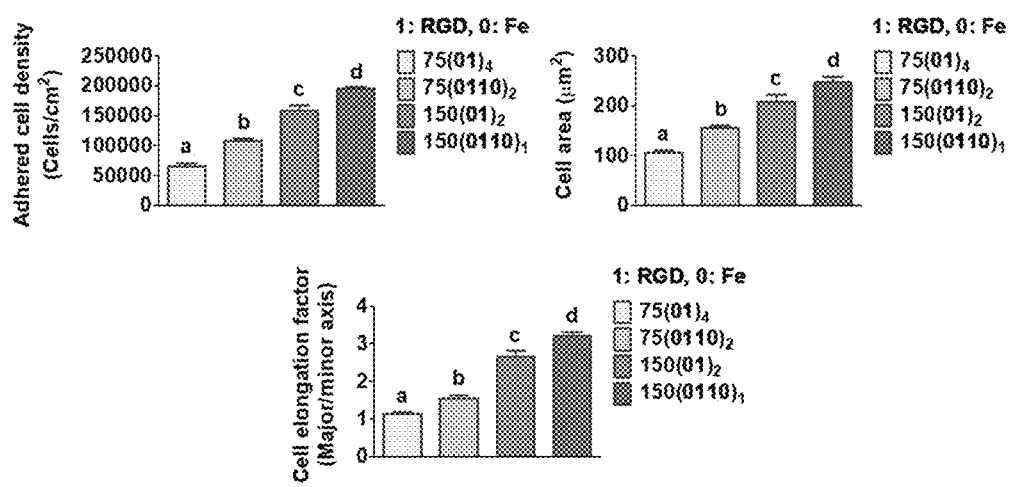

To check an influence of the nano-periodicity and ligand sequences of the nanobarcode according to the present invention to the adhesion of the macrophages, the following experiment was conducted, the result of which is represented in FIGS. 8 to 10.

The effect of tuning the ligand nano-periodicity in the ligand sequences for adhesion and phenotypic polarization of macrophages was evaluated. The substrate was subjected to sterilization under ultraviolet light for 1 hour prior to culture. Macrophages from passage 5 of RAW 264.7 (ATCC) at an approximate density of 90 kcells/$cm^2$ were seeded onto the sterilized substrate. Macrophages were then cultured at 37° C. under 5% $CO_2$ in basal medium containing high glucose DMEM, 10% heat-inactivated fetal bovine serum, and 50 U/Ml penicillin/streptomycin. The adhesion of macrophages was evaluated under the tuning of nano-periodicity alone in the nanobarcode of ligand sequences: $[30(01)_{10}]$, $[75(01)_4]$, $[150(01)_2]$, and $[300(01)_1]$ according to the present invention. The adhesion of macrophages was also evaluated under the tuning of both nano-periodicity and ligand sequences in the nanobarcode of the ligand sequences $[75(01)_4]$, $[75(0110)_2]$, $[150(01)_2]$, and $[150(0110)_1]$. The effect of nano-periodicity on the control of macrophage adhesion was evaluated by using the substrates with tunable nano-periodicity in Fe/Au sequences but without coupling RGD ligand as a comparative example.

M1 medium used for evaluation of the phenotypic polarization of macrophages was prepared by using a basal medium with 10 ng/mL each of lipopolysaccharide (LPS) and recombinant interferon-gamma (IFN-γ). M2 medium was prepared by using a basal medium with 20 ng/mL each of interleukin-4 (IL4) and interleukin-13 (IL-13). The adhesion-assisted M2 phenotypic polarization of the macrophages was evaluated with inhibitors of ROCK (50 μM Y27632), myosin II (10 μM blebbistatin), or actin polymerization (2 μg/mL of cytochalasin D).

FIG. 8 is an immunofluorescent confocal image of macrophages (after 24 hours) cultured by using the nanobarcode according to the exemplary embodiment of the present invention against F-actin, nucleus, and vinculin, and in this case, a scale bar represents 20 μm.

Referring to FIG. 8, immunofluorescent confocal images revealed that macrophages adhered more strongly with increasing (from 30 to 300) nano-periodicity presentation in ligand sequences. In particular, the macrophage adhesion density was found to increase by 68%, 180%, and 239% for $[75(01)_4]$, $[150(01)_2]$, and $[300(01)_1]$ groups, respectively, as compared to $[30(01)_{10}]$ group. Further, adherent macrophages showed more pervasive assembly of F-actin and vinculin across the cytoplasm and showed a significantly more elongated form according to an increase in ligand nano-periodicity. Through this, it can be seen that this is attributable to closer ligand presentation with increasing ligand nano-periodicity of the nanobarcode according to the present invention.

FIG. 9 is a result of an adhesion experiment of macrophages by tuning nano-periodicity in a nanobarcode (in the case where there is no RGD ligand binding) according to a Comparative Example of the present invention. In this case, the scale bar represents 20 μm. Referring to FIG. 9, it was confirmed that when the nano-periodicity in the Fe/Au sequences in the state where the RGD ligand is not coupled to the Au segments is turned, minimal levels of macrophage adhesion for all groups was yield with no significant differences. Through this, it can be seen that it is possible to efficiently alter the adhesion of macrophages by tuning the nano-periodicity of the RGD ligand sequences. In particular, it can be seen that when nano-periodicity increases in the ligand sequences, it is possible to effectively form robust adhesion structures in macrophages.

FIG. 10 is an immunofluorescent confocal image of macrophages (after 24 hours) cultured by using the nanobarcode (in which nano-periodicity and ligand sequences are tuned) according to the present invention against F-actin, nucleus, and vinculin, and in this case, a scale bar represents 20 μm. Referring to FIG. 10, the four periodically sequenced Fe/Au nanobarcodes of $[75(01)_4]$, $[75(0110)_2]$, $[150(01)_2]$, and $[150(0110)_1]$ were designed by tuning both the nano-periodicity and the ligand sequences to examine their effects on modulating adhesion of macrophages. In these groups, immunofluorescent confocal images showed that macrophages adhered more robustly with increasing nano-periodicity presentation in the ligand sequences. In particular, $[150(0110)_1]$ group showed significantly higher macrophage adhesion density, cell area, and cell elongation factor by 82%, 58%, and 108%, respectively, than $[75(0110)_2]$ group. Further, $[150(01)_2]$ group exhibited the assembly of substantially more robust adhesion structures than $[75(01)_4]$ group.

Further, even in the case where intra-nanobarcode ligand sequences alone were tuned without modulating ligand nano-periodicity, macrophage adhesion was controlled. Specifically, $[150(01)_2]$ group with ligand populated at the end sequence of nanobarcode exhibited significantly elevated macrophage adhesion density, cell area, and cell elongation factor by 47%, 34%, and 72%, respectively, as compared to $[75(0110)_2]$ group with ligand only populated in the inner sequence of nanobarcode. Through this, it can be seen that the lower inter-nanobarcode ligand spacing with ligand populated at the end sequence of the nanobarcode better facilitates cellular adhesion.

Accordingly, it is possible to control cell adhesion of macrophages by modulating the position of the sequence ligand of the nanobarcode and the spacing of the ligand.

Experimental Example 4

The experiment on whether the tuning of the nano-periodicity of the ligand sequences by using the nanobarcode according to the present invention controls the phenotypic polarization medium adhesion of macrophages was conducted as described below, and the results are represented in FIGS. 11 to 16.

The adhesive structures of macrophages are known to modulate their phenotypic polarization in the presence of M1 or M2 polarization stimulators. In particular, macrophages that develop robust adhesion structures, including the assembly of prevalent F-actin and vinculin in elongated shapes, are prone to activate their phenotypic polarization into regenerative/anti-inflammatory M2 state.

Figure 11:
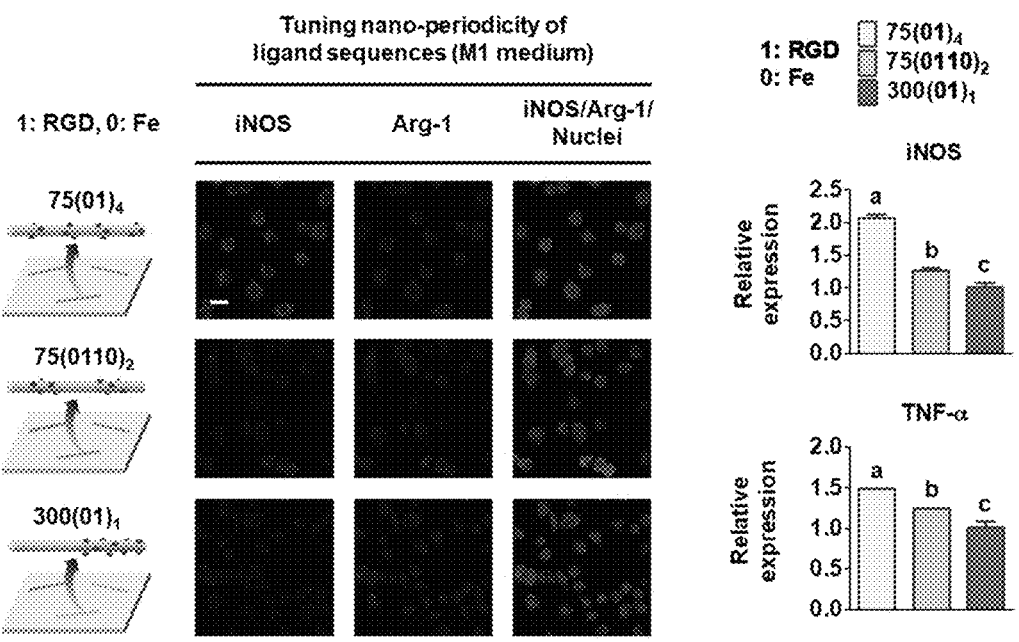
FIG. 11 is a diagram illustrating an experimental result of whether adhesion-dependent phenotypic polarization of macrophages is controlled by tuning nano-periodicity in the ligand sequences by using the nanobarcode according to the exemplary embodiment of the present invention.

FIG. 11 is a diagram illustrating an experimental result of whether adhesion-dependent phenotypic polarization of macrophages is controlled by tuning nano-periodicity in the ligand sequences by using the nanobarcode according to the exemplary embodiment of the present invention. Referring to FIG. 11, immunofluorescent confocal images revealed that macrophages gradually exhibited weaker iNOS fluorescence signals in M1-inducing medium, but exhibited stronger Arg-1 fluorescence signals in M2-inducing medium with increasing nano-periodicity presentation in the ligand sequences. Further, gene expression profiles corroborated the trend observed in the immunofluorescence. Macrophages showed significantly lower iNOS and TNF-α expression in M1-inducing medium, but showed higher Arg-1 and Ym1 expression proportionally with increasing nano-periodicity presentation in the ligand sequences. Quantitatively, the $[300(01)_1]$ group showed decreased iNOS expression by 20% and 51% and decreased TNF-α expression by 19% and 32%, as compared to the $[75(0110)_2]$ and $[75(01)_4]$ groups, respectively. Conversely, the $[300(01)_1]$ group showed increased Arg-1 expression by 35% and 107% and increased Ym1 expression by 185% and 483%, as compared with the $[75(0110)_2]$ and $[75(01)_4]$ groups, respectively.

Figure 12:
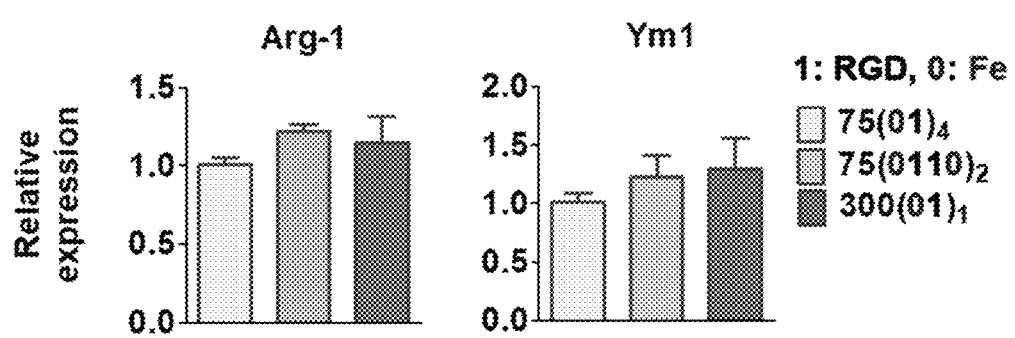
FIGS. 12 and 13 are diagrams illustrating experimental results for tuning nano-periodicity in ligand sequences when there is no stimulation medium matched with the polarization phenotype (that is, M1 expression in M2-stimulation medium (FIG. 12) and M2 expression in M1-stimulation medium (FIG. 13)) by using the nanobarcode according to the exemplary embodiment of the present invention.
Figure 13:
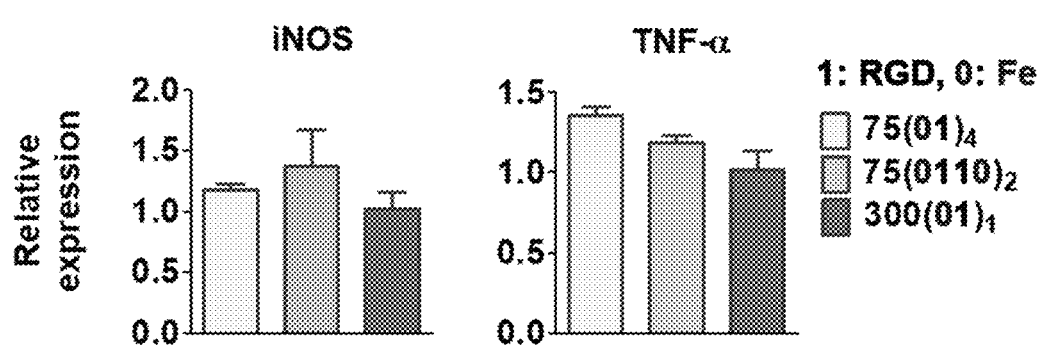

FIGS. 12 and 13 are diagrams illustrating experimental results for tuning nano-periodicity in ligand sequences when there is no stimulation medium matched with the polarization phenotype (that is, M1 expression in an M2-stimulation medium and M2 expression in an M1-stimulation medium) by using the nanobarcode of the present invention. Referring to FIG. 12, it was found that the tuning of the nano-periodicity in the ligand sequences under no presence of the stimulation medium matched with the polarization phenotype (that is, M1 expression in the M2-stimulation medium and M2 expression in the M1-stimulation medium) results in minimum iNOS and Arg-1 expression in immunofluorescence, and does not exhibit a meaningful difference in iNOS, TNF-α, Arg-1, and Ym1 expression.

Through this, overall, it can be seen that the high nano-periodicity in the ligand sequence promotes adhesion of the macrophages to activate the M2 phenotypic polarization while inhibiting M1 phenotypic polarization.

Figure 14:
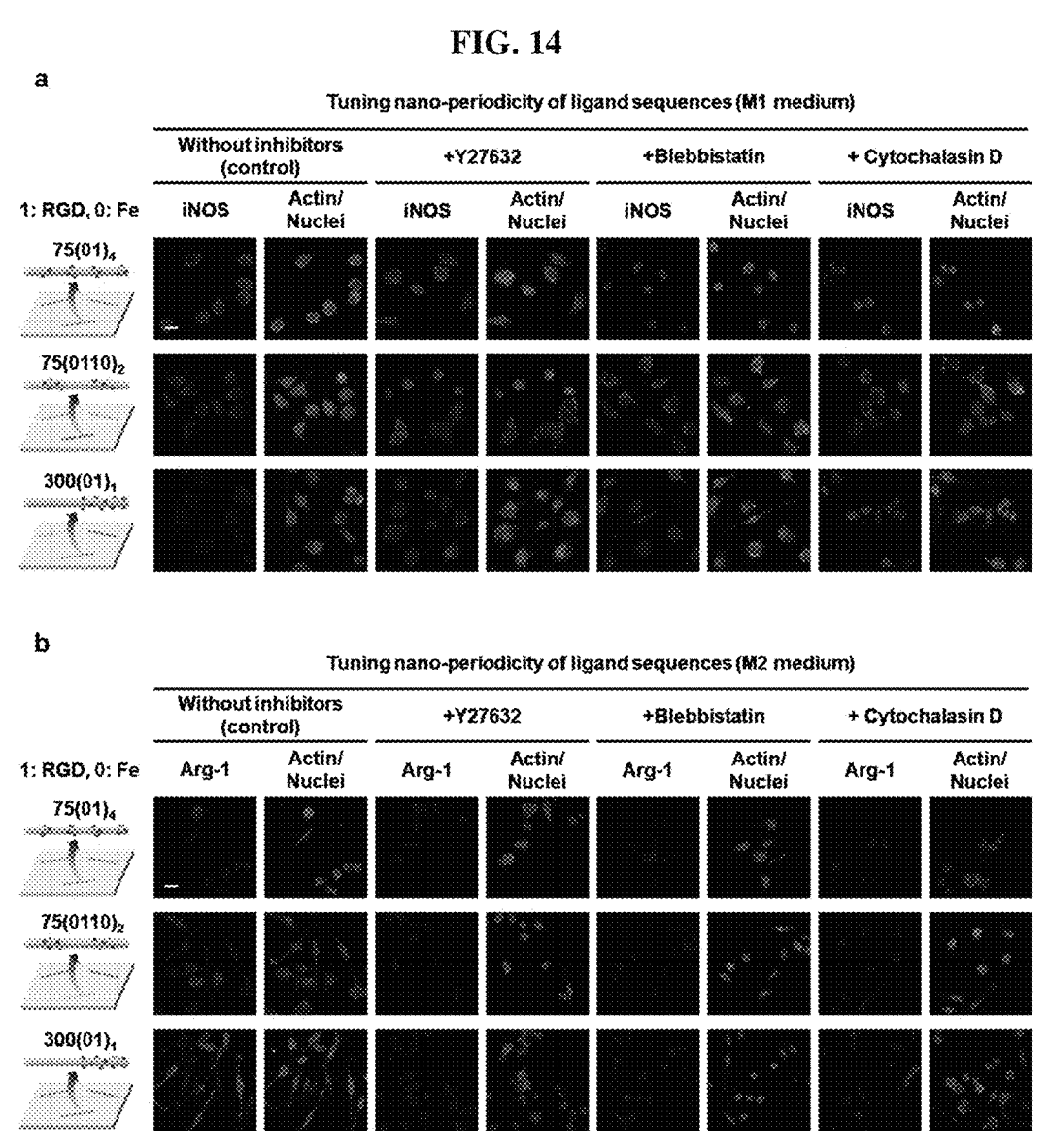

FIG. 14 is an immunofluorescent confocal image (a) for iNOS, F-actin, and nucleus cultured for 36 hours in the M1 polarization medium, and an immunofluorescent confocal image (b) for Arg-1, F-actin, and nucleus cultured in the M2 polarization medium with and without inhibitors for ROCK (Y27632), myosin II (blevisstatin), or actin polymerization (cytocalacin D), and in this case, a scale bar represents 20 μm.

Referring to FIG. 14, it can be seen that the high nano-periodicity in the ligand sequence promotes growth of robust adhesion structure to further facilitate the M2 phenotypic polarization while inhibiting M1 phenotypic polarization. In particular, the adhesion structure of the macrophages and the phenotypic polarization were evaluated by using a pharmacological inhibitor (Y 27632, blevisstatin, or cytocalacin D) that inhibits ROCK, myosin II, or actin polymerization.

Figure 15:
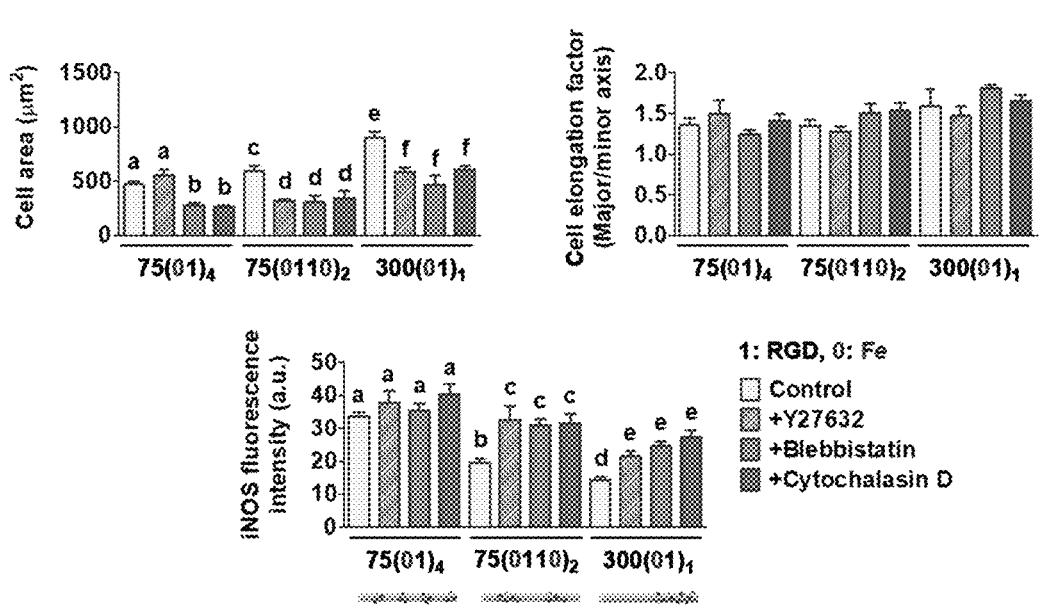
FIG. 15 is a graph illustrating a cell area, a cell elongation factor, and iNOS fluorescence intensity calculated based on the confocal immunofluorescence experimental result of FIG. 14.
Figure 16:
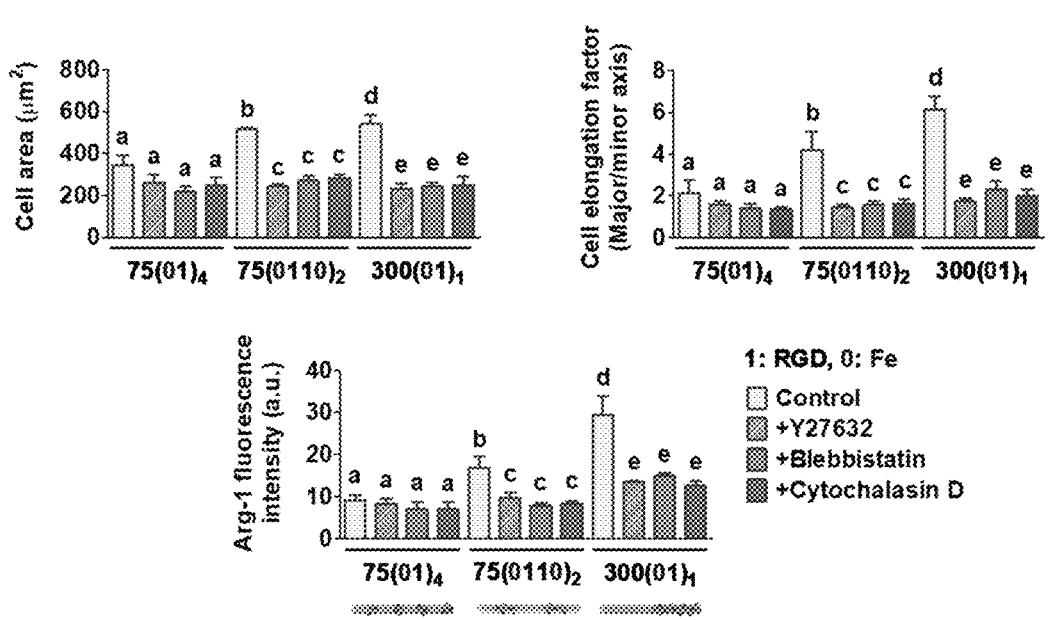
FIG. 16 is a graph illustrating a cell area, a cell elongation factor, and Arg-1 fluorescence intensity calculated based on the confocal immunofluorescence experimental result of FIG. 14.

Further, FIGS. 15 and 16 are graphs illustrating a cell area, a cell elongation factor, and iNOS fluorescence intensity or Arg-1 fluorescence intensity calculated based on the confocal immunofluorescence experimental result of FIG. 14.

Referring to FIGS. 14 and 15, in the immunofluorescent confocal image, the $[300(01)_1]$ group that is the macrophage having the highest nano-periodicity in the ligand sequence group showed the iNOS fluorescent signal increased by 50% by the inhibition of ROCK by Y27632 in the M1-inducing medium, resulting in the decrease in the cell area by 35%. Further, the $[300(01)_1]$ group showed the increasing iNOS fluorescence intensity by the inhibition of myosin II and actin polymerization by blevisstatin and cytocalacin D, respectively, resulting in the significant decrease in the cell area. Accordingly, it can be seen that the high nano-periodicity in the ligand sequence stimulates the robust adhesion of the macrophages to effectively inhibit the M1 phenotypic polarization.

Referring to FIGS. 14 and 16, in the M2-inducing medium, the $[300(01)_1]$ group showed the decrease in the cell area by 57%, the cell elongation factor by 72%, and Arg-1 fluorescence by 54% by the ROCK suppression. In particular, the $[300(01)_1]$ group significantly decreased the cell area, the cell elongation factor, and the Arg-1 fluorescence signal by inhibiting the actin polymerization with myosin II, blevisstatin, and cytocalacin D, respectively. Through this, it can be seen that the high nano-periodicity in the ligand sequence stimulates robust adhesion of the macrophages to effectively inhibit the M1 phenotypic polarization of the macrophages and promote the M2 phenotypic polarization of the macrophages.

Experimental Example 5

Figure 17:
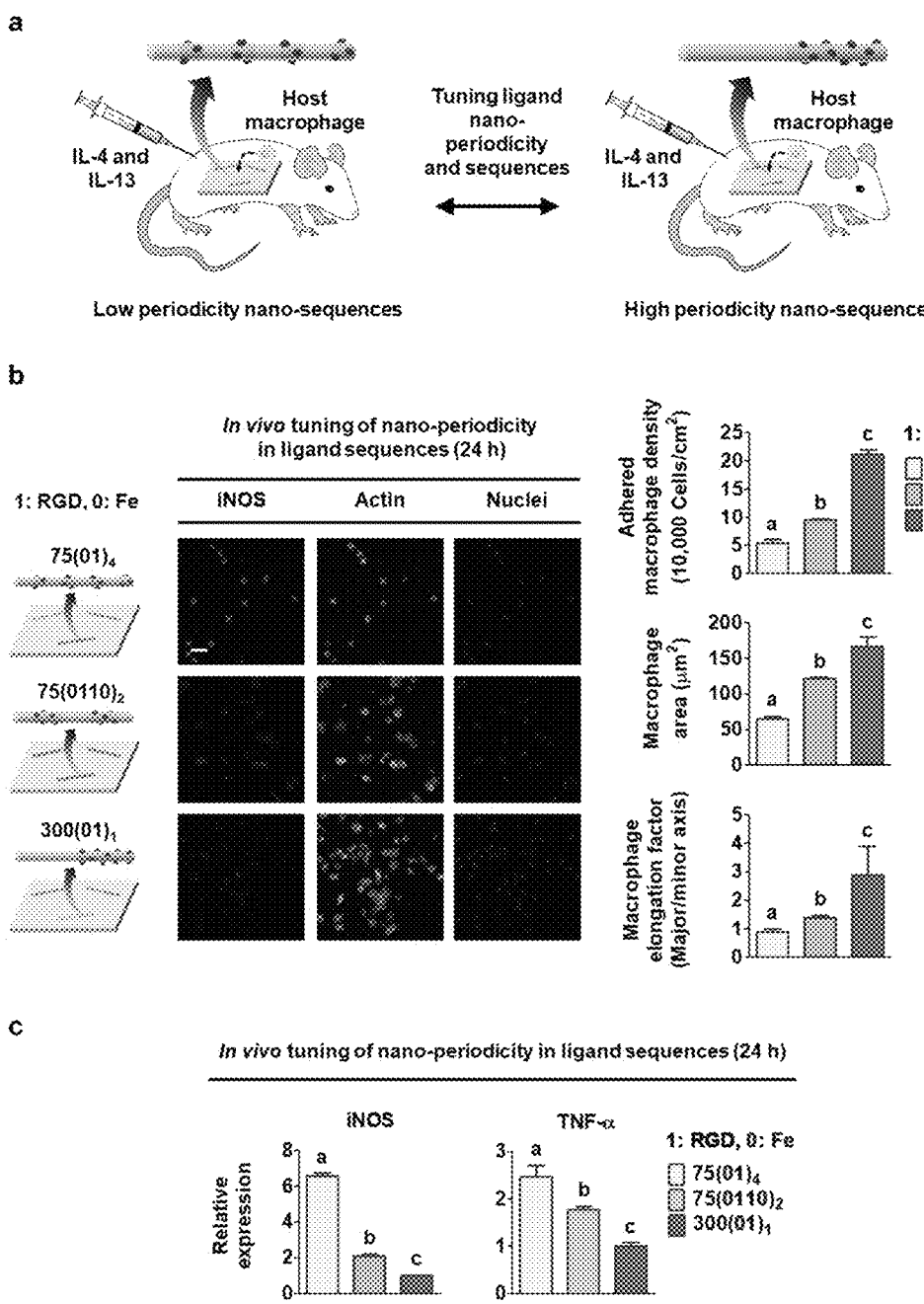
FIG. 17 is a diagram illustrating an experimental result of a control of adhesion and phenotypic polarization of host macrophage in vivo by using the nanobarcode according to the exemplary embodiment of the present invention.
Figure 18:
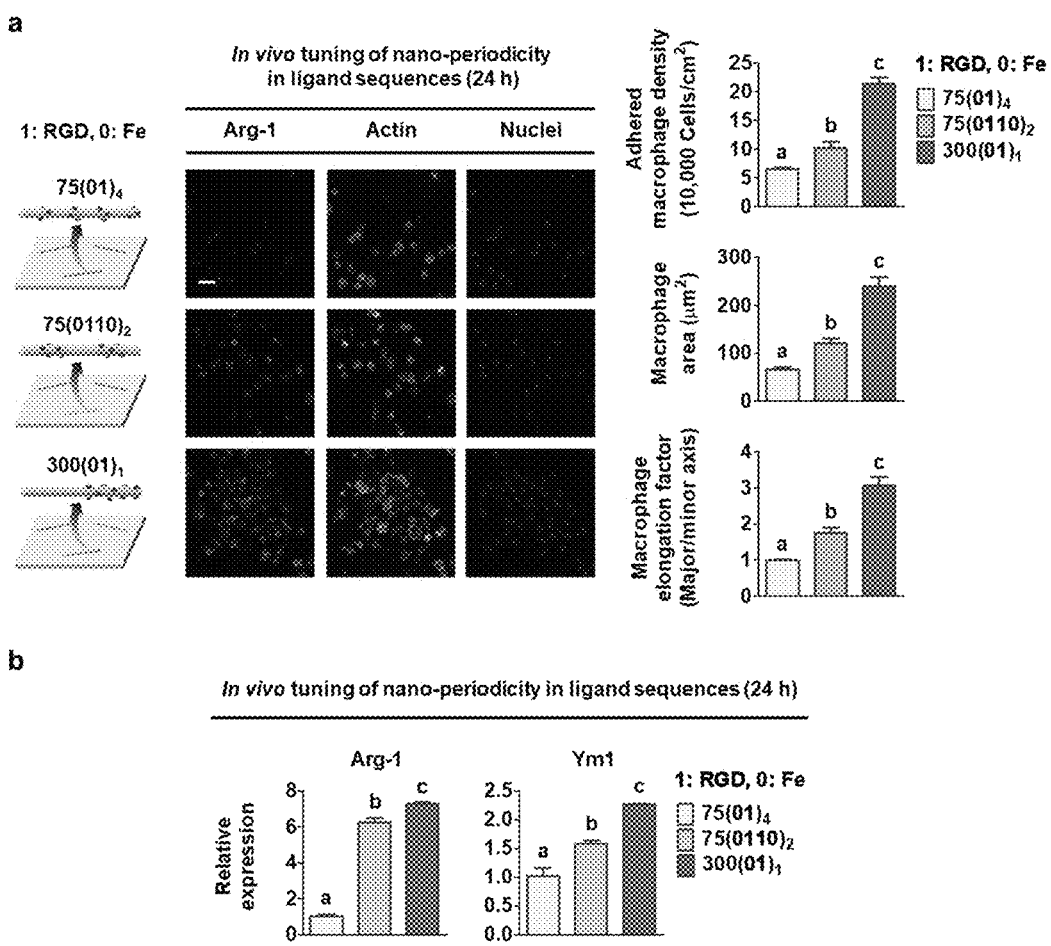
FIG. 18 is a diagram illustrating a result of an experiment in vivo by using the substrate including the nanobarcode according to the exemplary embodiment of the present invention, and a of FIG. 18 is an immunofluorescent confocal image of Arg-1, F-actin, and nuclei of host macrophages adhering to the substrate after 24 hours, and in this case, a scale bar represents 20 μm, and b of FIG. 18 is a graph illustrating a quantitative analysis result of adherent host cells in vivo in density, cell area, cell elongation factor (major/minor axis ratio) (n=10), and gene expression (n=3) of M2 phenotypic markers (Arg-1 and Ym1).
Figure 19:
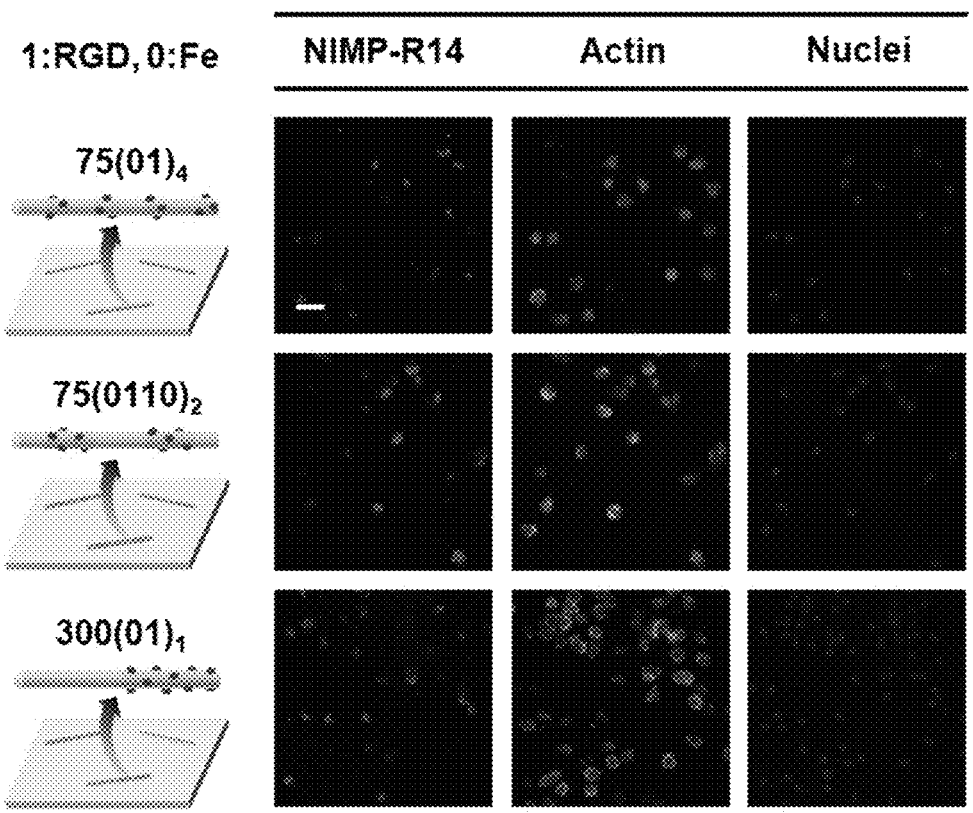
FIG. 19 is a result of in vivo adhesion of host neutrophils to a substrate exhibiting tunable nano-periodicity in ligand sequences by using the substrate including the nanobarcode according to the exemplary embodiment of the present invention.
Figure 19:
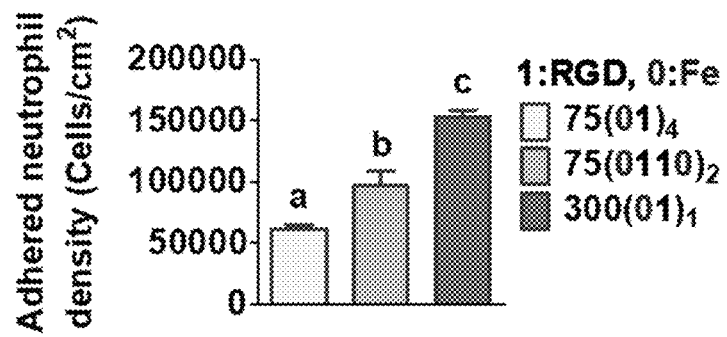

The following experiment was performed to confirm that the adhesion and phenotype of host macrophages in vivo are spatially controlled by using the nanobarcode according to the present invention, and the results thereof are represented in FIGS. 17 to 19.

FIG. 17 is a diagram illustrating an experimental result of the control of the adhesion and phenotype of the host macrophages in vivo by using the nanobarcode according to the present invention. a of FIG. 17 is a schematic diagram of the in vivo nano-periodicity tuning in the ligand sequences, and both interleukin-4 and interleukin-13 (M2 inducing agent) were injected onto the subcutaneously implanted substrate in vivo. b of FIG. 17 is an immunofluorescent confocal image of iNOS, F-actin, and the nuclei of host macrophages adhering to the substrate after 24 hours, and in this case, a scale bar represents 20 μm. c of FIG. 17 is a quantitative analysis result of the in vivo adhering host cells in the density of the M1 phenotypic markers (iNOS and TNF-α), cell area, cell elongation factor (major/minor axis ratio) (n=10), and gene expression (n=3).

a of FIG. 18 is an immunofluorescent confocal image of Arg-1, F-actin, and the nuclei of host macrophages adhering to the substrate after 24 hours, and in this case, a scale bar represents 20 μm. b of FIG. 18 is a graph of a quantitative analysis result of the in vivo adhering host cells in the density of the M2 phenotypic markers (Arg-1 and Ym1), cell area, cell elongation factor (major/minor axis ratio) (n=10), and gene expression (n=3).

Referring to FIGS. 17 and 18, the host response to the implanted material is dominated by functionally activated immune cell in which the phenotypic polarized macrophages play an important role. In relation to this, when the adherent and regenerative/anti-inflammatory phenotypic polarization of the host macrophages is controlled, it is possible to facilitate immune regulatory tissue polarization while inhibiting inflammation.

Further, adherence and phenotypic polarization of the recruited host macrophages were confirmed by immunofluorescence staining against host cells for actin, iNOS, or Arg-1. The immunofluorescent confocal images revealed that the adherent host macrophages had higher density and the gradually increasing cell area and cell elongation factor as the nano-periodicity presentation in the ligand sequences increases.

For example, the $[300(01)_1]$ group showed higher density of host macrophages by 120% and 299% than $[75(0110)_2]$ and $[75(01)_4]$ groups, respectively. Conversely, co-localization of iNOS and F-actin became gradually more predominant with significantly higher iNOS and TNF-α expression according to the decrease in the nano-periodicity presentation in the ligand sequences. In contrast, the co-localization of Arg-1 and F-actin became more predominant with significantly higher Arg-1 and Ym1 expression according to the increase in the nano-periodicity presentation in the ligand sequences. Quantitatively, the $[300(01)_1]$ group exhibited the increase in the Arg-1 expression by 17% and 624% and the increase in the Ym1 expression by 43% and 122% as compared to $[75(0110)_2]$ and $[75(01)_4]$ groups, respectively.

Through this, it can be seen that the in vivo tuning of the high nano-periodicity presentation in the ligand sequences promotes regenerative and inflammation-suppressive phenotypic polarization of the host macrophages to make the adhesion of the host macrophages easy.

FIG. 19 is a result of in vivo adhesion of host neutrophils to a substrate exhibiting tunable nano-periodicity in ligand sequences by using the substrate including the nanobarcode according to the present invention. a of FIG. 19 is an immunofluorescent confocal image of NIMP-R14, F-actin, and the nuclei of host macrophages adhering to the substrate after 24 hours, and in this case, a scale bar represents 20 μm. b of FIG. 19 is a graph of quantification results of in vivo adherent NIMP-R14-positive host neutrophils and both interleukin-4 and interleukin-13 were injected onto the subcutaneously implanted substrate in vivo representing the tunable nano-periodicity of the ligand sequences.

Referring to FIG. 19, the long-term host response to the implanted material is dominated by the phenotypic polarized macrophages having NIMP-R14-positive host neutrophils that appear in early acute inflammation.

What is claimed is:

1. A nanobarcode for controlling adhesion and polarization of macrophages comprising:
   a metallic nanowire comprising a first segment and a second segment, the first segment comprises iron (Fe) and the second segment comprises gold (Au); and
   an integrin ligand peptide comprising an Arg-Gly-Asp (RGD) attachment site bound to the second segment, wherein
   the nanobarcode comprises a rod-shaped structure which satisfies Equation 1, $$[L(M1M2)q] \qquad [\text{Equation 1}]$$

wherein
   M1 is the first segment,
   M2 is the second segment,
   q is the number of the first and second segments are repeated on the nanobarcode, wherein q is a whole number between 1 and 10,
   L is a total length of the q first and second segments, wherein L is a whole number between 30 and 300 nm,
   the controlling comprises tuning periodicity and sequences of the integrin ligand peptide, and
   the integrin ligand peptide comprises a thiol group and further wherein the thiol group is chemically bound to the second segment.

2. The nanobarcode of claim 1, wherein Equation 1 is selected from a group consisting of $[30(M_1M_2)_{10}]$, $[75(M_1M_2)_4]$, $[150(M_1M_2)_2]$, and $[300(M_1M_2)_1]$.

3. The nanobarcode of claim 1, wherein
   each of the first segment and the second segment comprises a rod-shaped structure, and
   a length of the first segment is the same as a length of the second segment.

4. The nanobarcode of claim 1, wherein
   the first segment further comprises a carboxylate.

5. The nanobarcode of claim 1, wherein
   the nanobarcode has a rod shape having a circular cross section with
   a diameter of 50 nm to 100 nm and
   a length of 200 to 1,000 nm.

* * * * *